(12) United States Patent
Kim et al.

(10) Patent No.: US 11,142,779 B2
(45) Date of Patent: *Oct. 12, 2021

(54) O-SUCCINYL HOMOSERINE TRANSFERASE VARIANT AND METHOD OF PRODUCING O-SUCCINYL HOMOSERINE USING THE SAME

(71) Applicant: CJ CheilJedang Corporation, Seoul (KR)

(72) Inventors: Kyungrim Kim, Seoul (KR); Jihyun Shim, Seoul (KR); Hyun Ah Kim, Seoul (KR); Yong Uk Shin, Seoul (KR); Peter Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/627,655

(22) PCT Filed: Jun. 29, 2018

(86) PCT No.: PCT/KR2018/007408
§ 371 (c)(1),
(2) Date: Dec. 30, 2019

(87) PCT Pub. No.: WO2019/004779
PCT Pub. Date: Jan. 3, 2019

(65) Prior Publication Data
US 2020/0332322 A1 Oct. 22, 2020

(30) Foreign Application Priority Data
Jun. 30, 2017 (KR) .......................... 10-2017-0083438

(51) Int. Cl.
*C12N 9/10* (2006.01)
*C12N 1/21* (2006.01)
*C12P 13/06* (2006.01)
*C12P 13/12* (2006.01)
*C12N 9/12* (2006.01)

(52) U.S. Cl.
CPC ................ *C12P 13/06* (2013.01); *C12N 9/12* (2013.01); *C12P 13/12* (2013.01)

(58) Field of Classification Search
None
See application file for complete search history.

(56) References Cited

U.S. PATENT DOCUMENTS

2015/0211034 A1    6/2015   Kim et al.

FOREIGN PATENT DOCUMENTS

| WO | 01/00843 A2 | 1/2001 |
| WO | 2008013432 A1 | 1/2008 |
| WO | 2010098629 A2 | 9/2010 |
| WO | 2015060649 A1 | 4/2015 |
| WO | 2016179545 A1 | 11/2016 |

OTHER PUBLICATIONS

GenPept Accession No. CCH69695, Jun. 2013, 2 pages (Year: 2013).*
Singh et al., Curr. Protein Pept. Sci. 18:1-11, 2017 (Year: 2017).*
Zhang et al., Structure 26:1474-1485, 2018 (Year: 2018).*
Mordukhova, Elena et al. "Stabilized homoserine o-succinyltransferases (MetA) or L-methionine partially recovers the growth defect in *Escherichia coli* lacking ATP-dependent proteases or the DnaK chaperone" BMC Microbiology 2013, 13:179 13 pages.
NCBI GenPept Accession No. WP 011013793.1, Jun. 2013.
EP 18823952.9 Extended European Search Report dated Feb. 3, 2021.

* cited by examiner

*Primary Examiner* — David Steadman
(74) *Attorney, Agent, or Firm* — Edwin S. Flores; Daniel J. Chalker; Chalker Flores, LLP

(57) ABSTRACT

Provided are an O-succinyl homoserine transferase variant, a polynucleotide encoding the variant, a microorganism comprising the variant, and a method of producing O-succinyl homoserine using the microorganism.

13 Claims, No Drawings
Specification includes a Sequence Listing.

O-SUCCINYL HOMOSERINE TRANSFERASE VARIANT AND METHOD OF PRODUCING O-SUCCINYL HOMOSERINE USING THE SAME

CROSS-REFERENCE TO RELATED APPLICATIONS

This application is the National Stage of International Application No. PCT/KR2018/007408, filed on Jun. 28, 2018 claiming the priority of KR 10-2017-0083438, filed on Jun. 30, 2017, the content of each of which is incorporated by reference herein.

TECHNICAL FIELD OF THE INVENTION

The present disclosure relates to an O-succinyl homoserine transferase variant, a polynucleotide encoding the variant, a microorganism comprising the variant, and a method of producing O-succinyl homoserine using the microorganism.

Incorporation-by-Reference of Materials Filed on Compact Disc

The present application includes a Sequence Listing which has been submitted in ASCII format via EFS-Web and is hereby incorporated by reference in its entirety. Said ASCII copy, created on Dec. 30, 2019, is named HANO1020US SeqList.txt and is 121 kilobytes in size.

Deposit of Biological Material

The following biological material has been deposited under the terms of the Budapest Treaty with the Korean Culture Center of Microoganisms, Yurim B/D, 45, Hongjenae-2ga-gil, Seodaemun-gu, Seoul 120-861 Republic of Korea, and given the following number:

Deposit Accession Number Date of Deposit
*Corynebacterium glutamicum* CA05-5132 KCCM12023P May 11, 2017

The microorganism has been deposited under conditions that assure that access to the microorganism will be available during the pendency of this patent application to one determined by the Commissioner of Patents and Trademarks to be entitled thereto under 37 C.F.R. § 1.14 and 35 U.S.C. § 122. The deposit is available as required by foreign patent laws in countries wherein counterparts of the subject application, or its progeny are filed. However, it should be understood that the availability of a deposit does not constitute a license to practice the subject invention in derogation of patent rights granted by government action.

BACKGROUND OF THE INVENTION

O-succinyl homoserine acts as a precursor of methionine which is a type of essential amino acids in a living body. Methionine is used as feed and food additives and further used as a synthetic raw material for medical solutions and medical supplies.

Methionine is produced through chemical synthesis and biological synthesis. Meanwhile, disclosed is a two-step process (WO/2008/013432), in which an L-methionine precursor is produced through fermentation, and then converted into L-methionine by an enzymatic conversion reaction.

In the two-step process, O-succinyl homoserine or O-acetyl homoserine is used as the methionine precursor, and for economical mass-production of methionine, it is very important to produce O-succinyl homoserine with high yield.

metA gene is a gene encoding homoserine O-succinyltransferase (MetA) which is an enzyme that conjugates a succinyl group of succinyl-coA to homoserine to produce O-succinyl homoserine, and metA gene is one of the most important genes in developing an O-succinyl homoserine-producing stain.

A strain accumulating O-succinyl homoserine may be prepared through deletion of metB gene encoding cystathionine gamma synthase in the methionine biosynthesis pathway. However, the O-succinylhomoserine-producing strain requires L-methionine. For this reason, the activity of homoserine O-succinyltransferase is inhibited through feedback inhibition by methionine which is added to a medium, and eventually, it is difficult to obtain O-succinyl homoserine at a high concentration.

Accordingly, many prior patents have focused their studies on the release of feedback inhibition of metA from a feedback control system. However, the homoserine O-succinyltransferase encoded by metA has problems in that the wild-type protein itself has low stability and introduction of a mutation for the release of feedback inhibition aggravates the instability. Accordingly, for the development of an O-succinyl homoserine-producing strain with high productivity, it is necessary to remove the feedback inhibition of the metA gene and to secure the enzyme stability.

Most microorganisms present in nature are known to utilize O-succinyl homoserine or O-acetyl homoserine as an intermediate for the biosynthesis of methionine. Generally, MetA produces O-succinyl homoserine and homoserine O-acetyltransferase (MetX) produces O-acetyl homoserine. Unlike MetA, MetX is not feedback-inhibited and has high enzyme stability.

SUMMARY OF THE INVENTION

Technical Problem

The present inventors have made intensive efforts to increase the production of O-succinyl homoserine, and as a result, they found a protein having O-succinyl homoserine-synthesizing activity, thereby completing the present disclosure.

Technical Solution

An object of the present disclosure is to provide a polypeptide having O-succinyl homoserine transferase activity, the peptide including substitution of an amino acid other than leucine for an amino acid at position 313 in an amino acid sequence of SEQ ID NO: 1.

Another object of the present disclosure is to provide a polynucleotide encoding the polypeptide.

Still another object of the present disclosure is to provide an O-succinyl homoserine-producing microorganism of the genus *Corynebacterium*, the microorganism comprising the polypeptide having the O-succinyl homoserine transferase activity.

Still another object of the present disclosure is to provide a method of producing O-succinyl homoserine, the method comprising the steps of culturing the microorganism in a medium; and isolating or collecting O-succinyl homoserine from the cultured microorganism or the medium.

Still another object of the present disclosure is to provide a method of producing L-methionine, the method comprising the steps of culturing the microorganism in a medium; and reacting the O-succinyl homoserine with sulfide.

Advantageous Effects

A variant of O-succinyl homoserine transferase protein according to the present disclosure may have enhanced O-succinyl homoserine conversion activity, as compared with a natural form thereof, thereby being widely applied to more efficient mass-production of 0-succinyl homoserine as an alternative to existing chemical synthesis pathways.

BEST MODE

Hereinafter, the present disclosure will be described in more detail.

Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

Further, one of ordinary skill in the art may recognize or identify many equivalents to certain aspects of the present disclosure described in this disclosure using only common experiments. Also, such equivalents are intended to be included in this disclosure.

To achieve the objects, one aspect of the present disclosure provides a novel polypeptide having O-succinyl homoserine transferase activity. The novel polypeptide variant may be a polypeptide having O-succinyl homoserine transferase activity, the polypeptide comprising substitution of an amino acid other than leucine for an amino acid at position 313 in an amino acid sequence derived from *Corynebacterium glutamicum*, specifically, in an amino acid sequence of SEQ ID NO: 1. Further, the polypeptide may comprise substitution of an amino acid other than leucine at position 313 in the amino acid sequence of SEQ ID NO: 1 and may have O-succinyl homoserine transferase activity. More specifically, the polypeptide may be a polypeptide having O-succinyl homoserine transferase activity, in which the polypeptide comprises substitution of arginine, cysteine, isoleucine, or lysine for the amino acid at position 313 in the amino acid sequence of SEQ ID NO: 1, but is not limited thereto.

Such a polypeptide variant is characterized by having enhanced O-succinyl homoserine transferase activity, as compared with the polypeptide having O-succinyl homoserine transferase activity of SEQ ID NO: 1.

As used herein, the term "O-succinyl homoserine transferase activity" refers to activity of converting homoserine into O-succinyl homoserine. The O-succinyl homoserine transferase collectively refers to an enzyme capable of converting succinyl CoA and L-homoserine as substrates into CoA and O-succinyl homoserine.

[Reaction Scheme]

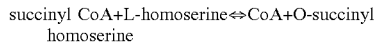

In the present disclosure, the O-succinyl homoserine transferase refers to an enzyme having O-succinyl homoserine transferase activity, which is obtained by substituting another amino acid for part of the amino acid sequence of MetX protein which is an O-acetyl homoserine transferase. The MetX protein may be MetX derived from the genus *Corynebacterium*, and more specifically, MetX having the amino acid sequence of SEQ ID NO: 1, which is derived from *Corynebacterium glutamicum*, but is not limited thereto. The sequence of the MetX protein is available from NCBI GenBank which is a known database.

In the present disclosure, various methods known in the art are applicable to a method of obtaining the O-succinyl homoserine transferase. For example thereof, the O-succinyl homoserine transferase may be obtained from a microorganism of the genus *Corynebacterium* which is widely used for enzyme expression, by using gene synthesis techniques based on codon optimization by which enzymes may be obtained in high yield, or by using methods of screening useful enzyme resources, based on the bioinformatics of massive amounts of genetic information about microorganisms, but is not limited thereto.

In the present disclosure, the O-succinyl homoserine transferase variant may be used interchangeably with "mutated O-succinyl homoserine transferase" or "variant O-succinyl homoserine transferase". Meanwhile, the variant may be a non-naturally occurring variant.

Specifically, the mutated O-succinyl homoserine transferase of the present disclosure may have substitution of an amino acid other than leucine for the amino acid residue at position 313 from the N-terminus of the genus *Corynebacterium* (*Corynebacterium* sp.)-derived MetX having the amino acid sequence represented by SEQ ID NO: 1. Specifically, the leucine amino acid residue at position 313 may be substituted with arginine, cysteine, isoleucine, or lysine, but is not limited thereto. The mutated O-succinyl homoserine transferase of the present disclosure may include a polypeptide comprising a variation at position 313 from the N-terminus of the amino acid sequence represented by SEQ ID NO: 1, wherein the variation includes substitution of an amino acid selected from the group consisting of arginine, cysteine, isoleucine, and lysine, and the polypeptide may have at least 85% homology or identity to SEQ ID NO: 1, but is not limited thereto.

Further, the polypeptide having the O-succinyl homoserine transferase activity of the present disclosure may be any one selected from the group consisting of amino acid sequences represented by SEQ ID NO: 59, SEQ ID NO: 67, SEQ ID NO: 75, and SEQ ID NO: 81, which are specifically amino acid sequences of polypeptides having O-succinyl homoserine transferase activity, in which the amino acid at position 313 from the N-terminus of SEQ ID NO: 1 is mutated to arginine, cysteine, isoleucine, or lysine, respectively, but are not limited thereto. The polypeptide may comprise any polypeptide having 50%, 60%, 70%, 75%, 80%, 85%, 90%, 95%, 97%, or 99% or more homology or identity to the above sequences without limitation, as long as the polypeptide comprises the above variation and has enhanced O-succinyl homoserine conversion activity, as compared with the wild-type.

Further, MetX of the present disclosure may be a MetX protein consisting of the amino acid sequence of SEQ ID NO: 1 or an amino acid sequence having 80% or more homology or identity thereto, but is not limited thereto. Specifically, the MetX protein of the present disclosure may include the protein of SEQ ID NO: 1 and a protein having at least 80% or more, 85% or more, specifically 90% or more, more specifically 95% or more, or much more specifically 99% or more homology or identity to the SEQ ID NO: 1.

As used herein, the term "polypeptide variant" refers to a polypeptide, of which one or more amino acids differ from the recited sequence in conservative substitutions and/or modifications, but it retains functions or properties of the polypeptide. Variant polypeptides differ from an identified sequence by substitution, deletion, or addition of several amino acids. Such variants may be generally identified by modifying one of the above polypeptide sequences and evaluating the properties of the modified polypeptide. In other words, ability of a variant may be increased, unchanged, or decreased, as compared with that of a native protein. Such variants may be generally identified by modifying one of the above polypeptide sequences and evaluating reactivity of the modified polypeptide. Further, some variants may include those in which one or more portions, such as an N-terminal leader sequence or transmembrane domain, have been removed. Other variants may include variants in which a portion has been removed from the N- and/or C-terminus of a mature protein. The term "variant" may also be used as a modification, modified protein, modified polypeptide, mutant, mutein, divergent, etc., and any term is not limited, as long as it is used in a sense of being mutated. Specifically, the variant includes a variant in which the activity of *Corynebacterium glutamicum*-derived O-succinyl homoserine transferase is efficiently improved by variation of the amino acids thereof, as compared with the wild-type.

As used herein, the term "conservative substitution" means substitution of one amino acid with another amino acid that has similar structural and/or chemical properties. The variant may have, for example, one or more conservative substitutions while retaining one or more biological activities. Such amino acid substitutions may be generally made on the basis of similarity in polarity, charge, solubility, hydrophobicity, hydrophilicity, and/or the amphipathic nature of residues. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan. Commonly, conservative substitution has little or no effect on the activity of the resulting polypeptide.

Further, variants may include another modification including deletion or addition of amino acids that have minimal influence on properties and a secondary structure of the polypeptide. For example, a polypeptide may be conjugated to a signal (or leader) sequence at the N-terminus of the protein, which co-translationally or post-translationally directs transfer of the protein. The polypeptide may also be conjugated to other sequence or a linker for identification, purification, or synthesis of the polypeptide. In other words, even though 'a protein or polypeptide having an amino acid sequence of a particular SEQ ID NO' is described herein, it is apparent that a protein having an amino acid sequence, part of which is deleted, modified, substituted, conservatively substituted, or added, may be used in the present disclosure, as long as it has activity identical or corresponding to that of the polypeptide composed of the amino acid sequence of the corresponding SEQ ID NO. For example, as long as a protein has activity identical or corresponding to that of the variant polypeptide, addition of a sequence that does not alter the function of the protein before and after the amino acid sequence, naturally occurring mutations, silent mutations or conservative substitutions thereof are not excluded. It is apparent that even though the polypeptide has such a sequence addition or mutation, it falls within the scope of the present disclosure.

Further, it is apparent that, due to codon degeneracy, a polynucleotide which may be translated into the protein comprising any one amino acid sequence selected from the group consisting of amino acid sequences of SEQ ID NO: 1, SEQ ID NO: 59, SEQ ID NO: 67, SEQ ID NO: 75, and SEQ ID NO: 81, or the protein having homology or identity thereto may also be included. Alternatively, a probe which may be produced from a known nucleotide sequence, for example, a sequence which hybridizes with a complementary sequence to all or a part of the polynucleotide sequence under stringent conditions to encode the protein having the O-succinyl homoserine transferase activity may also be included without limitation. The term "stringent conditions" mean conditions under which specific hybridization between polynucleotides is allowed. Such conditions are described in detail in a literature (e.g., J. Sambrook et al., supra). For example, the stringent conditions may include, for example, conditions under which genes having high homology or identity, 80% or higher, 85% or higher, specifically 90% or higher, more specifically 95% or higher, much more specifically 97% or higher, particularly specifically 99% or higher homology or identity are hybridized with each other and genes having homology or identity lower than the above homology or identity are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS.

Although a mismatch between nucleotides may occur due to the stringency of hybridization, it is required that the two nucleic acids have a complementary sequence. The term "complementary" is used to describe the relationship between nucleotide bases which may hybridize with each other. For example, with respect to DNA, adenosine is complementary to thymine and cytosine is complementary to guanine. Accordingly, the present disclosure may include not only the substantially similar nucleic acid sequences but also isolated nucleic acid fragments which are complementary to the entire sequence.

Specifically, the polynucleotide having homology or identity may be detected using hybridization conditions including the hybridization step at a Tm value of 55° C. and the conditions described above. Additionally, the Tm value may be 60° C., 63° C., or 65° C., but is not limited thereto, and may be appropriately controlled by one of ordinary skill in the art according to the purposes.

Appropriate stringency for the hybridization of polynucleotides depends on the length and degree of complementarity of the polynucleotides, and the variables are well-known in the art (see Sambrook et al., supra, 9.50-9.51, 11.7-11.8).

The 'homology' or 'identity' refers to the degree of relevance between two given amino acid sequences or nucleotide sequences, and may be expressed as a percentage.

The terms 'homology' and 'identity' may be often used interchangeably.

The sequence homology or identity of the conserved polynucleotide or polypeptide may be determined by standard alignment algorithms, and may be used with default gap penalties established by the used program. Substantially, homologous or identical sequences may hybridize under moderately or highly stringent conditions such that the full length of the sequence or at least about 50%, 60%, 70%, 80%, or 90% or more of the full-length may hybridize. In addition, contemplated are polynucleotides that contain degenerate codons in place of codons in the hybridization.

Whether or not any two polynucleotide or polypeptide sequences have homology, similarity, or identity may be determined using known computer algorithms such as the "FASTA" program, using, for example, the default parameters as in Pearson et al (1988)[Proc. Natl. Acad. Sci. USA 85]: 2444, or determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, BLAST of the National Center for Biotechnology Information database, or ClustalW may be used to determine homology, similarity, or identity.

Homology, similarity, or identity of polynucleotides or polypeptides may be determined, for example, by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids), which are similar, divided by the total number of symbols in the shorter of the two sequences. Default parameters for the GAP program may include: (1) a unary comparison matrix (containing a value of 1 for identities and 0 for non-identities) and the weighted comparison matrix of Gribskov et al (1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or gap open penalty of 10, gap extension penalty of 0.5); and (3) no penalty for end gaps. Therefore, as used herein, the term "homology" or "identity" represents relevance between sequences.

Another aspect of the present disclosure provides a polynucleotide encoding the polypeptide having the O-succinyl homoserine transferase activity.

As used herein, the term "polynucleotide" refers to a DNA or RAN strand having a predetermined length or more, which is a long chain polymer of nucleotides formed by linking nucleotide monomers via covalent bonds. More specifically, the polynucleotide refers to a polynucleotide fragment encoding the variant polypeptide.

In the present disclosure, the gene encoding the amino acid sequence of the O-succinyl homoserine transferase may be a gene of the variant O-succinyl homoserine transferase, specifically, derived from *Corynebacterium glutamicum*. Based on genetic code degeneracy, nucleotide sequences encoding the same amino acid sequence and variants thereof are also included in the present disclosure, for example, represented by SEQ ID NO: 60, SEQ ID NO: 68, SEQ ID NO: 76, or SEQ ID NO: 82, but are not limited thereto.

Additionally, as for the variant polynucleotide, based on the genetic code degeneracy, nucleotide sequences encoding the same amino acid sequence and variants thereof are also included in the present disclosure.

As still another aspect of the present disclosure, the present disclosure provides a host cell comprising the polynucleotide encoding the variant polypeptide, or a microorganism transformed with a vector including the polynucleotide encoding the variant polypeptide. Specifically, the introduction may be performed by transformation, but is not limited thereto.

Specifically, the microorganism comprising the polypeptide of the variant O-succinyl homoserine transferase may have enhanced productivity of O-succinyl homoserine without inhibiting growth of the host cell, as compared with a microorganism comprising the polypeptide of the wild-type O-succinyl homoserine transferase, and thus O-succinyl homoserine may be obtained from the microorganism with high yield.

As used herein, the term "vector" is a DNA construct that includes a nucleotide sequence of a polynucleotide encoding a desired protein operably linked to an appropriate regulatory sequence to enable expression of the desired protein in an appropriate host cell. The regulatory sequence may include a promoter capable of initiating transcription, any operator sequence for the regulation of such transcription, a sequence encoding an appropriate mRNA ribosome-binding domain, and a sequence regulating termination of transcription and translation. After the vector is transformed into the appropriate host cell, it may replicate or function independently of the host genome, and may be integrated into the genome itself.

The vector used in the present disclosure is not particularly limited, as long as it is able to replicate in the host cell, and any vector known in the art may be used. Examples of commonly used vectors may include a natural or recombinant plasmid, cosmid, virus, and bacteriophage. For instance, pWE15, M13, MBL3, MBL4, IXII, ASHII, APII, t10, t11, Charon4A, Charon21A, etc. may be used as a phage vector or cosmid vector. As a plasmid vector, pBR type, pUC type, pBluescriptll type, pGEM type, pTZ type, pCL type, pET type, etc. may be used. Specifically, pDZ, pACYC177, pACYC184, pCL, pECCG117, pUC19, pBR322, pMW118, pCC1BAC vector, etc. may be used, but is not limited thereto.

The vector applicable in the present disclosure is not particularly limited, and a known expression vector may be used. Further, the polynucleotide encoding the desired protein may be inserted into the chromosome using a vector for intracellular chromosomal insertion. The chromosomal insertion of the polynucleotide may be performed by any method known in the art, for example, homologous recombination, but is not limited thereto. A selection marker to confirm the chromosomal insertion may be further included. The selection marker is to select cells transformed with the vector, that is, to confirm insertion of the desired polynucleotide, and the selection marker may include markers providing selectable phenotypes, such as drug resistance, auxotrophy, resistance to cytotoxic agents, or expression of surface proteins. Since only cells expressing the selection marker are able to survive or to show different phenotypes under the environment treated with a selective agent, the transformed cells may be selected.

As used herein, the term "transformation" means the introduction of a vector including a polynucleotide encoding a desired protein into a host cell in such a way that the protein encoded by the polynucleotide is expressed in the host cell. As long as the transformed polynucleotide may be expressed in the host cell, it may be integrated into and placed in the chromosome of the host cell, or it may exist extrachromosomally, or irrespective thereof. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette includes a promoter operably linked to the polynucleotide, transcriptional termination signals, ribosome binding sites, and translation termination signals. The expression cassette may be in the form of a self-replicable expression vector. Also, the polynucleotide as it is may be introduced into the host cell and operably linked to sequences required for expression in the host cell, but is not limited thereto. A method of performing the transformation may include any method of introducing nucleic acids into a cell, and the transformation may be performed by selecting an appropriate standard technique as known in the art according to the host cell. For example, the method may include electroporation, calcium phosphate ($Ca(H_2PO_4)_2$, $CaHPO_4$, or $Ca_3(PO_4)_2$) precipitation, calcium chloride ($CaCl_2$) precipitation, microinjection, a polyethylene glycol (PEG) method, a DEAE-dextran method, a cationic liposome method, and a lithium acetate-DMSO method, etc., but is not limited thereto.

As used herein, the term "operably linked" means a functional linkage between the polynucleotide sequence encoding the desired protein of the present disclosure and a promoter sequence which initiates and mediates transcription of the polynucleotide. The operable linkage may be prepared using a genetic recombinant technology known in the art, and site-specific DNA cleavage and linkage may be prepared using cleavage and linking enzymes, etc., in the art, but is not limited thereto.

As used herein, the term "O-succinyl homoserine-producing microorganism" refers to a microorganism that naturally has O-succinyl homoserine-producing ability or a microorganism that is prepared by providing a mother strain having no O-succinyl homoserine-producing ability with the O-succinyl homoserine-producing ability.

The O-succinyl homoserine-producing microorganism may be a cell or microorganism which may include the polynucleotide encoding the variant polypeptide or which may express the variant polypeptide by transformation with the vector including the polynucleotide encoding the variant polypeptide. With respect to the objects of the present disclosure, the host cell or microorganism may be any microorganism, as long as it is able to produce O-succinyl homoserine by including the variant MetX polypeptide. Specific examples thereof may include microorganisms of the genus *Escherichia*, the genus *Serratia*, the genus *Erwinia*, the genus *Enterobacteria*, the genus *Salmonella*, the genus *Streptomyces*, the genus *Pseudomonas*, the genus *Brevibacterium*, and the genus *Corynebacterium*, specifically, a microorganism of the genus of *Corynebacterium*, and more specifically, *Corynebacterium glutamicum*, but are not limited thereto.

As used herein, the term "O-succinyl homoserine-producing microorganism of the genus *Corynebacterium*" refers to a microorganism of the genus *Corynebacterium* having O-succinyl homoserine-producing ability naturally or through mutation. It has been known that a culture of the microorganism of the genus *Corynebacterium* includes O-succinyl homoserine. However, its O-succinyl homoserine-producing ability is remarkably low, and genes involved in the production mechanism or mechanisms thereof have not been revealed. Therefore, in the present disclosure, the microorganism of the genus *Corynebacterium* having the O-succinyl homoserine-producing ability refers to a natural form of the microorganism itself, or a microorganism of the genus *Corynebacterium* having the O-succinyl homoserine-producing ability which is improved by insertion of a foreign gene related to the O-succinyl homoserine production mechanism or by enhancement or inactivation of the activity of an endogenous gene.

In the present disclosure, "the microorganism of the genus *Corynebacterium*" may be specifically *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, etc., but is not limited thereto. More specifically, in the present disclosure, the microorganism of the genus *Corynebacterium* may be *Corynebacterium glutamicum*, of which cell growth and survival are less influenced even though exposed to high levels of O-succinyl homoserine.

In the microorganism, activity of at least one protein selected from the group consisting of cystathionine synthase, O-acetyl homoserine (thiol)-lyase, and homoserine kinase may be inactivated. In other words, activity of one protein selected therefrom, activities of two proteins selected therefrom, or activities of all the three proteins may be inactivated.

As used herein, the term "inactivation" of the protein activity is a concept including weakening of the activity, as compared with its intrinsic activity, or having no activity.

The inactivation of the protein activity may be achieved by applying various methods well-known in the art. Examples of the methods may include a method of deleting the entirety or part of the protein-encoding gene on the chromosome, including the case when the protein activity is eliminated; a method of substituting the protein-encoding gene on the chromosome with a gene which is mutated to reduce the enzyme activity; a method of introducing a variation into the expression control sequence of the protein-encoding gene on the chromosome; a method of replacing the expression control sequence of the protein-encoding gene with a sequence having weak activity or no activity (e.g., a method of replacing the promoter of the gene with a promoter weaker than the intrinsic promoter); a method of deleting the entirety or part of the protein-encoding gene on the chromosome; a method of introducing an antisense oligonucleotide (e.g., antisense RNA), which inhibits the translation from the mRNA into a protein via a complementary binding to a transcript of the gene on the chromosome; a method of making the attachment of a ribosome impossible by forming a secondary structure by artificially adding a complementary sequence to the SD sequence on the front end of the SD sequence of the protein-encoding gene; a reverse transcription engineering (RTE) method of adding a promoter to be reversely transcribed on the 3' terminus of the open reading frame (ORF) of the corresponding sequence; or a combination thereof, but are not particularly limited thereto.

Specifically, the method of deleting part or the entirety of the protein-encoding gene may be executed by replacing the polynucleotide encoding the endogenous desired protein within the chromosome with a polynucleotide or a marker gene having a partially deleted nucleotide sequence, via a vector for chromosomal insertion into the microorganism. For example thereof, a method of deleting the gene by homologous recombination may be used, but is not limited thereto. Additionally, the "part", although it may vary depending on the kinds of polynucleotide, may be appropriately determined by those skilled in the art, and it may be specifically 1 nucleotide to 300 nucleotides, more specifically 1 nucleotide to 100 nucleotides, and even more specifically 1 nucleotide to 50 nucleotides, but is not particularly limited thereto.

Further, the method of modifying the expression control sequence may be performed by inducing a modification in the expression control sequence via deletion, insertion, non-conservative or conservative substitution, or a combination thereof so as to further inactivate the activity of the expression control sequence, or by replacing the sequence with a nucleotide sequence having a weaker activity. The expression control sequence may include a promoter, an operator sequence, a sequence encoding a ribosome-binding domain, and a sequence for regulating transcription and translation, but is not limited thereto.

Furthermore, the method of modifying the nucleotide sequence on the chromosome may be performed by inducing a modification in the sequence via deletion, insertion, conservative or non-conservative substitution, or a combination thereof so as to further inactivate the activity of the protein, or by replacing the sequence with a nucleotide sequence which is improved to have a weaker activity or a nucleotide sequence which is improved to have no activity, but is not limited thereto. Specifically, in the microorganism, at least one gene selected from the group consisting of a cystathionine gamma synthase-encoding metB gene, an O-acetyl homoserine (thiol)-lyase-encoding metY gene which is an O-succinyl homoserine degradation pathway, and a homoserine kinase-encoding thrB gene may be further deleted or weakened.

As used herein, the term "deletion" refers to a type of removal, within the chromosome, of a part or the entirety of a nucleotide sequence region of a desired gene from the nucleotide sequence corresponding to the start codon to that of the stop codon, or a part or the entirety of the nucleotide sequence of a regulatory region thereof.

As used herein, the term "weakening" refers to removal or reduction of intracellular activity of one or more enzymes which are encoded by the corresponding DNA in a microorganism strain. For example, protein expression may be weakened by modifying a nucleotide sequence of a promoter region or 5'-UTR of a gene, or protein activity may be weakened by introducing a mutation in the ORF region of the corresponding gene.

Further, the microorganism of the genus *Corynebacterium* may be an O-succinyl homoserine-producing microorganism of the genus *Corynebacterium*, in which aspartokinase activity is further enhanced, as compared with a non-variant microorganism.

As used herein, the term "enhancement of the activity of the protein" refers to introduction of the activity of the protein, or increase of the activity of the protein, as compared with its intrinsic activity. The "introduction" of the activity means occurrence of activity of a specific polypeptide which is naturally or artificially not possessed by the microorganism.

As used herein, the term "increase" of the activity of the protein, as compared with its intrinsic activity, means that the activity is improved, as compared with the intrinsic activity of the protein of the microorganism or the activity before modification. The term "intrinsic activity" refers to activity of a specific protein originally possessed by a parent strain or unmodified microorganism before changing its trait, when the trait of the microorganism is changed due to genetic variation caused by natural or artificial factors. It may be used interchangeably with the activity before modification.

Specifically, in the present disclosure, the enhancement of activity may be performed by:

1) increasing the copy number of the polynucleotide encoding the protein, 2) modifying the expression control sequence for increasing the expression of the polynucleotide, 3) modifying the polynucleotide sequence on the chromosome for enhancing the activity of the protein, 4) introducing a foreign polynucleotide exhibiting the activity of the protein or a variant polynucleotide in which the polynucleotide is codon-optimized, or 5) modifying for the enhancement by a combination thereof, but is not limited thereto.

1) The increase of the copy number of the polynucleotide may be, but is not particularly limited to, performed in a form in which the polynucleotide is operably linked to a vector, or by inserting the polynucleotide into the chromosome of a host cell. Specifically, the increase of the copy number of the polynucleotide within the chromosome of the host cell may be performed by introducing a vector into a host cell, the vector which may replicate and function regardless of a host cell and to which the polynucleotide encoding the protein of the present disclosure is operably linked, or may be performed by introducing a vector into a host cell, the vector which may insert the polynucleotide into the chromosome of a host cell and to which the polynucleotide is operably linked.

Next, 2) the modification of the expression control sequence for increasing the expression of the polynucleotide may be, but is not particularly limited to, performed by inducing a modification on the sequence through deletion, insertion, non-conservative or conservative substitution of the nucleotide sequence, or a combination thereof to further enhance the activity of the expression control sequence, or by replacing the polynucleotide sequence with a nucleotide sequence having a stronger activity. The expression control sequence includes, but is not particularly limited to, a promoter, an operator sequence, a sequence encoding a ribosome-binding site, and a sequence regulating the termination of transcription and translation.

A strong exogenous promoter, instead of the original promoter, may be connected to the upstream region of the expression unit of the polynucleotide. Examples of the strong promoter may include CJ7 promoter (Korean Patent No. 0620092 and WO2006/065095), lysCP1 promoter (WO2009/096689), EF-Tu promoter, groEL promoter, aceA or aceB promoter, etc., but is not limited thereto. Furthermore, 3) the modification of the polynucleotide sequence on the chromosome may be, but is not particularly limited to, performed by inducing a modification on the expression control sequence through deletion, insertion, non-conservative or conservative substitution of the polynucleotide sequence, or a combination thereof to further enhance the activity of the polynucleotide sequence, or by replacing the polynucleotide sequence with a polynucleotide sequence which is improved to have a stronger activity.

Further, 4) the introduction of the foreign polynucleotide sequence may be performed by introducing a foreign polynucleotide sequence encoding a protein showing the activity identical/similar to that of the above protein or by introducing a codon-optimized variant polynucleotide thereof into a host cell. Any foreign polynucleotide sequence may be used without limitation in the origin or sequence thereof, as long as it shows the activity identical/similar to that of the above protein. Further, the foreign polynucleotide may be introduced into the host cell, after optimizing its codons such that that optimized transcription and translation may occur in the host cell. The introduction may be carried out by a known transformation method which is appropriately selected by those skilled in the art, and the protein may be produced by expression of the introduced polynucleotide in the host cell, and as a result, its activity may be increased.

Lastly, 5) the method of modifying for the enhancement by a combination of 1) to 4) may be performed by applying one or more of the methods of increasing the copy number of the polynucleotide encoding the protein, modifying the expression control sequence for increasing the expression of the polynucleotide, modifying the polynucleotide sequence on the chromosome, and modifying a foreign polynucleotide exhibiting the activity of the protein or a variant polynucleotide in which the codons thereof are codon-optimized.

In the present disclosure, the sequences of the genes or the polynucleotides are available from a database such as National Center for Biotechnology Information (NCBI).

As still another aspect of the present disclosure, the present disclosure provides a method of producing O-succinyl homoserine, the method comprising the steps of culturing the above-described microorganism; and collecting O-succinyl homoserine from the cultured microorganism or the culture medium.

As still another aspect of the present disclosure, the present disclosure provides a method of producing L-methionine, the method comprising the steps of culturing the above-described microorganism; and reacting the cultured microorganism or the O-succinyl homoserine with sulfide.

Specifically, the step of reacting with sulfide means producing L-methionine from 0-succinyl homoserine using any known method. For example, L-methionine may be produced by reacting O-succinyl homoserine with methyl mercaptan as the sulfide, or methionine may be produced by a stepwise reaction through production of cystathionine by reacting O-succinyl homoserine with cysteine as the sulfide. Further, to improve the reaction rate and yield, a catalyst or an enzyme may be added, or reaction may be allowed in a microorganism including enzymes.

The 'O-succinyl homoserine' may be a fermentation broth containing O-succinyl homoserine produced by the above-described microorganism of the present disclosure or a purified form thereof. In addition, the 'sulfide' may be for example, methyl mercaptan. The methyl mercaptan refers to all of methyl mercaptan derivatives capable of providing sulfur atoms, such as a liquefied sodium methyl mercaptan ($CH_3S$—Na) form, and gaseous or liquefied methyl mercaptan ($CH_3SH$) form, as well as a methyl mercaptan including dimethylsulfide (DMS) which is disclosed in Patent Publication WO2010/098629, etc.

The method of producing L-methionine may be readily determined by those skilled in the art under optimized culture conditions and enzyme activation conditions known in the art.

A specific culture method and medium are the same as described above.

Further, the method of producing L-methionine may further comprise the step of isolating or collecting O-succinyl homoserine from the microorganism cultured in the culturing step or the medium.

It is apparent to those skilled in the art that the "O-succinyl homoserine" of the present disclosure may include all of O-succinyl homoserine itself and salts thereof.

In the above method, the step of culturing the microorganism may be performed by a known batch culture, continuous culture, or fed-batch culture method, but is not particularly limited thereto. Regarding the culturing conditions, proper pH (i.e. pH of 5 to 9, specifically pH of 6 to 8, and most specifically pH of 6.8) may be adjusted using a basic compound (e.g., sodium hydroxide, potassium hydroxide, or ammonia) or an acidic compound (e.g., phosphoric acid or sulfuric acid), and an aerobic condition may be maintained by adding oxygen or an oxygen-containing gas mixture to the culture, but are not particularly limited thereto. The culture temperature may be maintained at 20° C. to 45° C., and specifically at 25° C. to 40° C., and the microorganism may be cultured for about 10 hours to about 160 hours, but is not limited thereto. The O-succinyl homoserine produced by the above culturing may be secreted to the medium or remain within the cells.

Additionally, in the culture medium to be used, carbon sources, such as sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid), may be used individually or in a mixture thereof, but are not limited thereto. Nitrogen sources, such as nitrogen-containing organic compounds (e.g., peptone, yeast extract, meat juice, malt extract, corn steep liquor, soybean flour, and urea) or inorganic compounds (e.g., ammonium sulfate, ammonium chloride, ammonium phosphate, ammonium carbonate, and ammonium nitrate), may be used individually or in a mixture thereof, but are not limited thereto. Potassium sources, such as potassium dihydrogen phosphate, dipotassium hydrogen phosphate, or sodium-containing salts corresponding thereto, may be used individually or in a mixture thereof, but are not limited thereto. Additionally, other essential growth-stimulating substances including metal salts (e.g., magnesium sulfate or iron sulfate), amino acids, and vitamins may be included in the medium.

A method of collecting the O-succinyl homoserine or L-methionine which is produced in the culturing step of the present disclosure may be to collect the desired amino acid from the culture broth using an appropriate method known in the art according to the culture method. For example, centrifugation, filtration, anion exchange chromatography, crystallization, HPLC, etc., may be used, and the desired O-succinyl homoserine or L-methionine may be collected from the medium or microorganism using an appropriate method known in the art.

MODE FOR DISCLOSURE

Hereinafter, the present disclosure will be described in more detail with reference to Examples. However, these Examples are for illustrative purposes only, and the scope of the present disclosure is not intended to be limited by these Examples.

Example 1: Construction of MetX Plasmid Having O-Acetyl Homoserine Transferase Activity To amplify an O-acetyl homoserine transferase (MetX)-encoding gene, BamHI restriction sites were inserted into both ends of primers (SEQ ID NOS: 5 and 6) to amplify from a promoter region (about 300 bp from the upstream of start codons) to a terminator region (about 100 bp from the downstream of stop codons), based on the reported WT (Wild type)-derived sequence.

TABLE 1

| SEQ ID NO: | Primer | Sequence (5'-3') |
|---|---|---|
| 5 | Primer 1 | GGATCCCCTCGTTGTTCACCCAGCAACC |
| 6 | Primer 2 | GGATCCCAAAGTCACAACTACTTATGTTAG |

After denaturation at 95° C. for 5 minutes, the PCR was carried out for a total of 30 cycles under the following conditions: denaturation at 95° C. for 30 seconds; annealing at 55° C. for 30 seconds; and polymerization at 72° C. for 90 seconds. Thereafter, the polymerization reaction was carried out at 72° C. for 7 minutes. As a result, a DNA fragment of 1546 bp of the coding region of the metX gene was obtained. A pECCG117 (Korean Patent No. 10-0057684) vector and the metX DNA fragment were treated with a restriction enzyme BamHI, and ligated with each other using DNA ligase, and cloned, thereby obtaining a plasmid, which was designated as pECCG117-metX WT.

Example 2: Construction of Variant MetX Plasmid Having O-Succinyl Homoserine Transferase Activity Novel metX variation sites were selected, and an amino acid at position 313 in an amino acid sequence of SEQ ID NO: 1 was substituted with an amino acid other than leucine.

More specifically, to prepare a variant vector, in which the amino acid at position 313 of O-acetyl homoserine transferase was substituted with another amino acid, using the pECCG117-metX WT plasmid constructed in Example 1 as a template, a pair of primers (SEQ ID NOS: 7 and 8) was designed.

TABLE 2

| SEQ ID NO: | Primer | Sequence (5'-3'') |
|---|---|---|
| 7 | Primer 3 | GTAGATACCGATATTCGGTACCCCTACCACCAG |
| 8 | Primer 4 | CTGGTGGTAGGGGTACCGAATATCGGTATCTAC |

The primers and a site-directed mutagenesis kit (stratagene, USA) were used to prepare a metX variant gene. L313R variant plasmid, based on the wild-type plasmid WT, was designated as WT_L313R.

Example 3: Comparative Experiment of Substrate Specificity and Activity of Variant MetX Having O-Succinyl Homoserine Transferase Activity To compare activity of variant metX producing a large amount of O-succinyl homoserine, a strain in which homoserine was accumulated and availability of produced O-succinyl homoserine was deleted was prepared. A strain, in which metB gene encoding cystathionine gamma synthase which is involved in the O-succinyl homoserine degradation pathway and metY gene encoding O-acetyl homoserine (thiol)-lyase which is involved in the O-succinyl homoserine degradation pathway were deleted, was prepared. First, to delete the metB gene, a pair of primers (SEQ ID NOS: 9 and 10) for amplification of 5'-upstream region of metB gene and a pair of primers (SEQ ID NOS: 11 and 12) for amplification of 3'-downstream region of metB gene were designed, based on the nucleotide sequence of WT-derived metB gene. XbaI restriction sites (underlined) were inserted into each end of the primers of SEQ ID NOS: 9 and 12.

TABLE 3

| SEQ ID NO: | Primer | Sequence (5'-3') |
|---|---|---|
| 9 | Primer 5 | <u>TCTAGA</u>TGCGCTGATTATCTCACC |

TABLE 3-continued

| SEQ ID NO: | Primer | Sequence (5'-3') |
|---|---|---|
| 10 | Primer 6 | ACTGGTGGGTCATGGTTGCATATGAGATCAACTCCTGTAA |
| 11 | Primer 7 | TTACAGGAGTTGATCTCATATGCAACCATGACCCACCAGT |
| 12 | Primer 8 | <u>TCTAGA</u>CCTTGAAGTTCTTGACTG |

PCR was performed using the chromosome of WT as a template and the primers of SEQ ID NO: 9 and SEQ ID NO: 10, SEQ ID NO: 11 and SEQ ID NO: 12. After denaturation at 95° C. for 5 minutes, the PCR was carried out for a total of 30 cycles under the following conditions: denaturation at 95° C. for 30 seconds; annealing at 55° C. for 30 seconds; and polymerization at 72° C. for 90 seconds. Thereafter, the polymerization reaction was carried out at 72° C. for 7 minutes. As a result, a DNA fragment of 450 bp of 5'-upstream region of metB gene and a DNA fragment of 467 bp of 3'-downstream region of metB gene were obtained.

PCR was performed using the amplified two kinds of DNA fragments as a template and primers of SEQ ID NO: 9 and SEQ ID NO: 12. After denaturation at 95° C. for 5 minutes, the PCR was carried out for a total of 30 cycles under the following conditions: denaturation at 95° C. for 30 seconds; annealing at 55° C. for 30 seconds; and polymerization at 72° C. for 3 minutes. Thereafter, the polymerization reaction was carried out at 72° C. for 7 minutes. As a result, a DNA fragment of 917 bp including only the upstream and downstream fragments by deletion of the middle of metB gene was amplified.

pDZ vector and the DNA fragment of 917 bp were treated with a restriction enzyme XbaI, and then ligated with each other using DNA ligase, and cloned, thereby obtaining a plasmid, which was designated as pDZ-ΔmetB.

The pDZ-ΔmetB vector was introduced into WT strain by an electric pulse method, and then a transformant strain was selected on a selection medium containing 25 mg/L of kanamycin. WTΔmetB strain in which metB gene was deleted by the DNA fragment inserted into the chromosome by a secondary recombination process (cross-over) was obtained.

To delete the metY gene which is another O-succinyl homoserine degradation pathway, a pair of primers (SEQ ID NOS: 13 and 14) for amplification of 5'-upstream region of metY gene and a pair of primers (SEQ ID NOS: 15 and 16) for amplification of 3'-downstream region of metY gene were designed, based on the nucleotide sequence of WT-derived metY gene. XbaI restriction sites (underlined) were inserted into each end of the primers of SEQ ID NOS: 13 and 16.

TABLE 4

| SEQ ID NO: | Primer | Sequence (5'-3') |
|---|---|---|
| 13 | Primer 9 | <u>TCTAGA</u>AGTAGCGTTGCTGTACAC |
| 14 | Primer 10 | ATCAATGGTCTCGATGCCCATATGGCATTTGGAGGTCCTTAAG |
| 15 | Primer 11 | CTTAAGGACCTCCAAATGCCATATGGGCATCGAGACCATTGAT |
| 16 | Primer 12 | <u>TCTAGA</u>TGGAACCGTTGCAACCAC |

PCR was performed using the chromosome of WT as a template and the primers of SEQ ID NO: 13 and SEQ ID NO: 14, SEQ ID NO: 15 and SEQ ID NO: 16. After denaturation at 95° C. for 5 minutes, the PCR was carried out for a total of 30 cycles under the following conditions: denaturation at 95° C. for 30 seconds; annealing at 55° C. for 30 seconds; and polymerization at 72° C. for 90 seconds. Thereafter, the polymerization reaction was carried out at 72° C. for 7 minutes. As a result, a DNA fragment of 512 bp of 5'-upstream region of metY gene and a DNA fragment of 520 bp of 3'-downstream region of metY gene were obtained.

PCR was performed using the amplified two kinds of DNA fragments as a template and primers of SEQ ID NO: 13 and SEQ ID NO: 16. After denaturation at 95° C. for 5 minutes, the PCR was carried out for a total of 30 cycles under the following conditions: denaturation at 95° C. for 30 seconds; annealing at 55° C. for 30 seconds; and polymerization at 72° C. for 3 minutes. Thereafter, the polymerization reaction was carried out at 72° C. for 7 minutes. As a result, a DNA fragment of 1032 bp including only the upstream and downstream fragments by deletion of the middle of metY gene was amplified.

pDZ vector and the DNA fragment of 1032 bp were treated with a restriction enzyme XbaI, and then ligated with each other using DNA ligase, and cloned, thereby obtaining a plasmid, which was designated as pDZ-ΔmetY.

The pDZ-ΔmetY vector was introduced into the prepared WTΔmetB strain by an electric pulse method, and then a transformant strain was selected on a selection medium containing 25 mg/L of kanamycin. WTΔmetBΔmetY strain in which metY gene was deleted by the DNA fragment inserted into the chromosome by a secondary recombination process (cross-over) was obtained.

To maximize the O-succinyl homoserine production, a pair of primers (SEQ ID NOS: 19 and 20) for amplifying 5'-upstream region and a pair of primers (SEQ ID NOS: 21 and 22) for amplifying 3'-downstream region around the variation site was designed to construct a variant-introducing vector for lysC gene (SEQ ID NO: 18) encoding WT-derived aspartokinase (SEQ ID NO: 17). The primers of SEQ ID NOS: 19 and 22 were inserted into the XbaI restriction sites (underlined) at each end, and the primers of SEQ ID NOS: 20 and 21 were allowed to place the nucleotide substitution variation (underlined) at the region which was designed to cross-over with each other.

TABLE 5

| SEQ ID NO: | Primer | Sequence (5'-3') |
|---|---|---|
| 19 | Primer 13 | TCCTCTAGAGCTGCGCAGTGTTGAATACG |
| 20 | Primer 14 | CACCGACATCATCTTCACCTGCC |
| 21 | Primer 15 | GGCAGGTGAAGATGATGTCGGTG |
| 22 | Primer 16 | GACTCTAGAGTTCACCTCAGAGACGATTA |

PCR was performed using the chromosome of WT as a template and primers of SEQ ID NO: 19 and SEQ ID NO: 20, SEQ ID NO: 21 and SEQ ID NO: 22. After denaturation at 95° C. for 5 minutes, the PCR was carried out for a total of 30 cycles under the following conditions: denaturation at 95° C. for 30 seconds; annealing at 55° C. for 30 seconds; and polymerization at 72° C. for 30 seconds. Thereafter, the polymerization reaction was carried out at 72° C. for 7 minutes. As a result, a DNA fragment of 509 bp of the 5'-upstream region and a DNA fragment of 520 bp of the 3'-downstream region around the lysC gene variation were obtained.

PCR was performed using the amplified two kinds of DNA fragments as a template and primers of SEQ ID NO: 19 and SEQ ID NO: 22. After denaturation at 95° C. for 5 minutes, the PCR was carried out for a total of 30 cycles under the following conditions: denaturation at 95° C. for 30 seconds; annealing at 55° C. for 30 seconds; and polymerization at 72° C. for 60 seconds. Thereafter, the polymerization reaction was carried out at 72° C. for 7 minutes. As a result, a DNA fragment of 1011 bp including the lysC gene variation (SEQ ID NO: 24) encoding the aspartokinase variant (SEQ ID NO: 23) in which threonine at position 311 was substituted with isoleucine was amplified.

pDZ vector (Korean Patent No. 0924065) which is not replicable in *Corynebacterium glutamicum* and the DNA fragment of 1011 bp were treated with a restriction enzyme XbaI, and ligated with each other using DNA ligase, and cloned, thereby obtaining a plasmid, which was designated as pDZ-lysC(T311I).

The pDZ-lysC(T311I) vector was introduced into WTΔmetBΔmetY by an electric pulse method (Appl. Microbiol. Biothcenol. (1999) 52:541-545), and then a transformant strain was selected on a selection medium containing 25 mg/L of kanamycin. WTΔmetBΔmetY, lysC(T311I) strain in which nucleotide variation was introduced into lysC gene by the DNA fragment inserted into the chromosome by a secondary recombination process (cross-over) was obtained, and the strain was designated as *Corynebacterium glutamicum* WTΔmetBΔmetY, lysC(T311I).

The pECCG117-metX WT and pECCG117-metX WT_L313R vectors prepared in Examples 1 and 2 were introduced into WTΔmetBΔmetY prepared as above by the electric pulse method, and then each transformant strain was selected on a selection medium containing 25 mg/L of kanamycin.

To compare O-acetyl homoserine (O-AH) and O-succinyl homoserine (O—SH)-producing abilities of the prepared strains, they were cultured by the following method, and O-acetyl homoserine and O-succinyl homoserine concentrations in culture media were analyzed.

Each one platinum loop of the strains was inoculated in a 250 ml-corner baffle flask containing 25 ml of the following medium, and then cultured at 37° C. and 200 rpm under shaking for 20 hours. O-acetyl homoserine and O-succinyl homoserine concentrations were analyzed by HPLC, and the analyzed concentrations were shown in Table 6.

<Composition of Medium (pH 7.0)>

100 g of glucose, 40 g of $(NH_4)_2SO_4$, 2.5 g of soybean protein, 5 g of corn steep solids, 3 g of urea, 1 g of $KH_2PO_4$, 0.5 g of $MgSO_4.7H_2O$, 100 μg of biotin, 1000 μg of thiamine HCl, 2000 μg of calcium pantothenate, 3000 μg of nicotinamide, 30 g of $CaCO_3$, 0.3 g of L-methionine (per 1 liter of distilled water).

TABLE 6

| | O-acetyl homoserine (g/L) | | | O-succinyl homoserine (g/L) | | |
|---|---|---|---|---|---|---|
| Strain | Batch 1 | Batch 2 | Batch 3 | Batch 1 | Batch 2 | Batch 3 |
| WTΔmetBΔmetY, lysC(T311I)/ pECCG117-metXWT | 2.0 | 2.2 | 2.1 | 0.01 | 0.03 | 0.01 |
| WTΔmetBΔmetY, | | | | | | |

TABLE 6-continued

| | O-acetyl homoserine (g/L) | | | O-succinyl homoserine (g/L) | | |
|---|---|---|---|---|---|---|
| Strain | Batch 1 | Batch 2 | Batch 3 | Batch 1 | Batch 2 | Batch 3 |
| lysC(T311I)/ pECCG117-metXWT_L313R | 0.05 | 0.06 | 0.04 | 1.2 | 1.1 | 1.0 |

Referring to Table 6, it was confirmed that the strain introduced with the control metX WT plasmid produced O-acetyl homoserine, whereas the strain introduced with the metX variant plasmid produced O-succinyl homoserine. In other words, the substrate specificity of the transferase was changed in the strain introduced with the variant, and as a result, O-succinyl homoserine was produced.

Further, the prepared WTΔmetBΔmetY, lysC(T311I)/pECCG117-metX WT_L313R strain was designated as CA05-5132, and then deposited at the Korean Culture Center of Microorganisms which is the international depository authority under the Budapest Treaty on May 11, 2017 with the Accession No. KCCM12023P.

Example 4: Preparation of MetX Variant Through Saturated Mutagenesis and Evaluation of O-Acetyl Homoserine-Producing Ability To prepare variants in which another amino acid was substituted at the metX variation site showing high O-succinyl homoserine-producing ability, saturated mutagenesis was used. 18 kinds of variants in which the amino acid at position 313 of metX was substituted with another amino acid were prepared, and the plasmid prepared in Example 1 was used as a template. Each variant, substituted amino acids, and SEQ ID NOs. of the primers used in each variant are shown in the following Table 7.

TABLE 7

| Plasmid variant | Amino acid substitution | SEQ ID NO: of primer |
|---|---|---|
| Variation at 313 | L313R | SEQ ID NOS: 7, 8 |
| | L313F | SEQ ID NOS: 25, 26 |
| | L313S | SEQ ID NOS: 27, 28 |
| | L313Y | SEQ ID NOS: 29, 30 |
| | L313C | SEQ ID NOS: 31, 32 |
| | L313P | SEQ ID NOS: 33, 34 |
| | L313H | SEQ ID NOS: 35, 36 |
| | L313Q | SEQ ID NOS: 37, 38 |
| | L313I | SEQ ID NOS: 39, 40 |
| | L313T | SEQ ID NOS: 41, 42 |
| | L313N | SEQ ID NOS: 43, 44 |
| | L313K | SEQ ID NOS: 45, 46 |
| | L313V | SEQ ID NOS: 47, 48 |
| | L313A | SEQ ID NOS: 49, 50 |
| | L313D | SEQ ID NOS: 51, 52 |
| | L313E | SEQ ID NOS: 53, 54 |
| | L313G | SEQ ID NOS: 55, 56 |
| | L313W | SEQ ID NOS: 57, 58 |

Specifically, the primers suggested in Table 2 and a site-directed mutagenesis kit (Stratagene, USA) were used to prepare variant metX genes. Each of the prepared variant plasmids was introduced into WTΔmetBΔmetY, lysC (T311I) strain, and a flask test was performed in the same manner as in Example 4. The results are shown in the following Table 8.

TABLE 8

| Strain | Mutation site | O-acetyl homoserine (g/L) | | | O-succinyl homoserine (g/L) | | |
|---|---|---|---|---|---|---|---|
| | | Batch 1 | Batch 2 | Batch 3 | Batch 1 | Batch 2 | Batch 3 |
| WTΔmetBΔmetY, lysC(T311I)/ pECCG117-metXWT | | 2.0 | 2.2 | 2.1 | 0.01 | 0.03 | 0.01 |
| WTΔmetBΔmetY, lysC(T311I)/ pECCG117-metXWT_L313R SEQ ID NO: 59 | L313R | 0.05 | 0.06 | 0.04 | 1.2 | 1.1 | 1.0 |
| WTΔmetBΔmetY, lysC(T311I)/ pECCG117-metX WT_L313FSEQ ID NO: 61 | L313F | 2.0 | 2.3 | 2.0 | 0.02 | 0.01 | 0.02 |
| WTΔmetBΔmetY, lysC(T311I)/ pECCG117-metXWT_L313S SEQ ID NO: 63 | L313S | 2.0 | 1.9 | 2.4 | 0.00 | 0.01 | 0.01 |
| WTΔmetBΔmetY, lysC(T311I)/ pECCG117-metXWT_L313Y SEQ ID NO: 65 | L313Y | 2.2 | 2.3 | 1.8 | 0.03 | 0.01 | 0.03 |
| WTΔmetBΔmetY, lysC(T311I)/ pECCG117-metXWT_L313C SEQ ID NO: 67 | L313C | 1.3 | 1.2 | 1.0 | 0.7 | 0.5 | 0.4 |
| WTΔmetBΔmetY, lysC(T311I)/ pECCG117-metXWT_L313P SEQ ID NO: 69 | L313P | 1.6 | 1.5 | 1.8 | 0.02 | 0.02 | 0.01 |
| WTΔmetBΔmetY, lysC(T311I)/ pECCG117-metXWT_L313H SEQ ID NO: 71 | L313H | 1.3 | 1.5 | 1.6 | 0.03 | 0.01 | 0.01 |
| WTΔmetBΔmetY, lysC(T311I)/ pECCG117-metXWT_L313Q SEQ ID NO: 73 | L313Q | 1.5 | 1.9 | 2.0 | 0.01 | 0.02 | 0.01 |
| WTΔmetBΔmetY, lysC(T311I)/ pECCG117-metXWT_L313I SEQ ID NO: 75 | L313I | 2.0 | 2.1 | 2.2 | 0.6 | 0.5 | 0.5 |
| WTΔmetBΔmetY, lysC(T311I)/ pECCG117-metXWT_L313T SEQ ID NO: 77 | L313T | 1.7 | 2.0 | 1.8 | 0.02 | 0.02 | 0.01 |

TABLE 8-continued

| Strain | Mutation site | O-acetyl homoserine (g/L) | | | O-succinyl homoserine (g/L) | | |
|---|---|---|---|---|---|---|---|
| | | Batch 1 | Batch 2 | Batch 3 | Batch 1 | Batch 2 | Batch 3 |
| WTΔmetBΔmetY, lysC(T311I)/pECCG117-metXWT_L313N SEQ ID NO: 79 | L313N | 1.9 | 2.2 | 2.1 | 0.01 | 0.00 | 0.01 |
| WTΔmetBΔmetY, lysC(T311I)/pECCG117-metXWT_L313K SEQ ID NO: 81 | L313K | 1.2 | 1.4 | 1.0 | 0.9 | 0.7 | 0.8 |
| WTΔmetBΔmetY, lysC(T311I)/pECCG117-metXWT_L313V SEQ ID NO: 83 | L313V | 1.9 | 1.5 | 1.8 | 0.02 | 0.03 | 0.01 |
| WTΔmetBΔmetY, lysC(T311I)/pECCG117-metXWT_L313A SEQ ID NO: 85 | L313A | 2.1 | 1.8 | 2.0 | 0.01 | 0.01 | 0.04 |
| WTΔmetBΔmetY, lysC(T311I)/pECCG117-metXWT_L313D SEQ ID NO: 87 | L313D | 2.0 | 2.2 | 1.8 | 0.02 | 0.02 | 0.03 |
| WTΔmetBΔmetY, lysC(T311I)/pECCG117-metXWT_L313E SEQ ID NO: 89 | L313E | 2.1 | 2.2 | 1.9 | 0.03 | 0.01 | 0.01 |
| WTΔmetBΔmetY, lysC(T311I)/pECCG117-metXWT_L313G SEQ ID NO: 91 | L313G | 2.3 | 2.1 | 2.1 | 0.04 | 0.02 | 0.01 |
| WTΔmetBΔmetY, lysC(T311I)/pECCG117-metXWT_L313W SEQ ID NO: 93 | L313W | 2.0 | 1.6 | 1.9 | 0.02 | 0.03 | 0.04 |

Referring to Table 3, it was confirmed that most variants did not produce O-succinyl homoserine, whereas the variant (L313R), (L313C), (L313I), or (L313K) having the amino acid variation at position 313 of metX produced O-succinyl homoserine at higher levels than the wild-type, respectively. In other words, when the amino acid at position 313 of the amino acid sequence of SEQ ID NO: 1 is substituted with arginine, cysteine, isoleucine, or lysine, substrate specificity for succinyl CoA may be provided, and as a result, O-succinyl homoserine may be produced.

Taken together, the results suggest that the variants of the present disclosure may increase production of O-succinyl homoserine.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

[Deposit Number]

Deposit Authority: Korean Culture Center of Microorganisms

Accession Number: KCCM12023P

Date of Deposit: May 11, 2017

SEQUENCE LISTING

```
<160> NUMBER OF SEQ ID NOS: 94

<210> SEQ ID NO 1
<211> LENGTH: 377
<212> TYPE: PRT
<213> ORGANISM: Corynebacterium glutamicum
<220> FEATURE:
<221> NAME/KEY: MISC_FEATURE
<223> OTHER INFORMATION: metX

<400> SEQUENCE: 1

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60
```

```
Trp Trp Ala Asp Leu Leu Gly Pro Gly Lys Ala Ile Asn Thr Asp Ile
 65                  70                  75                  80

Tyr Cys Val Ile Cys Thr Asn Val Ile Gly Cys Asn Gly Ser Thr
             85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
            115                 120                 125

Asp Ala Leu Gly Ile Thr Thr Val Ala Ala Val Leu Gly Gly Ser Met
            130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
                180                 185                 190

Trp His Glu Gly Asn Tyr Tyr Glu Ser Gly Cys Asn Pro Ala Thr Gly
            195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
            275                 280                 285

Arg Gly Gly Leu Asn Lys Ala Leu Glu Ser Ile Lys Val Pro Val Leu
    290                 295                 300

Val Ala Gly Val Asp Thr Asp Ile Leu Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
            355                 360                 365

Pro Ser Thr Tyr Ile Glu Phe Tyr Ile
            370                 375

<210> SEQ ID NO 2
<211> LENGTH: 1134
<212> TYPE: DNA
<213> ORGANISM: Corynebacterium glutamicum
<220> FEATURE:
<221> NAME/KEY: misc_feature
<223> OTHER INFORMATION: metX

<400> SEQUENCE: 2
atgcccaccc tcgcgccttc aggtcaactt gaaatccaag cgatcggtga tgtctccacc      60
gaagccggag caatcattac aaacgctgaa atcgcctatc accgctgggg tgaataccgc    120
gtagataaag aaggacgcag caatgtcgtt ctcatcgaac acgccctcac tggagattcc    180
aacgcagccg attggtgggc tgacttgctc ggtcccggca agccatcaa cactgatatt    240
```

-continued

```
tactgcgtga tctgtaccaa cgtcatcggt ggttgcaacg gttccaccgg acctggctcc    300
atgcatccag atggaaattt ctggggtaat cgcttccccg ccacgtccat tcgtgatcag    360
gtaaacgccg aaaacaatt cctcgacgca ctcggcatca ccacggtcgc cgcagtactt     420
ggtggttcca tgggtggtgc ccgcacccta gagtgggccg caatgtaccc agaaactgtt    480
ggcgcagctg ctgttcttgc agtttctgca cgcgccagcg cctggcaaat cggcattcaa    540
tccgcccaaa ttaaggcgat tgaaaacgac caccactggc acgaaggcaa ctactacgaa    600
tccggctgca acccagccac cggactcggc gccgcccgac gcatcgccca cctcacctac    660
cgtggcgaac tagaaatcga cgaacgcttc ggcaccaaag cccaaaagaa cgaaaaccca    720
ctcggtccct accgcaagcc cgaccagcgc ttcgccgtgg aatcctactt ggactaccaa    780
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatattttgt accctacca ccagcaagaa     960
cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caacccttcg acctacatcg agttctacat ctaa          1134
```

<210> SEQ ID NO 3
<211> LENGTH: 379
<212> TYPE: PRT
<213> ORGANISM: Pseudomonas aeruginosa
<220> FEATURE:
<221> NAME/KEY: MISC_FEATURE
<223> OTHER INFORMATION: metX1

<400> SEQUENCE: 3

```
Met Pro Thr Val Phe Pro Asp Asp Ser Val Gly Leu Val Ser Pro Gln
1               5                   10                  15

Thr Leu His Phe Asn Glu Pro Leu Glu Leu Thr Ser Gly Lys Ser Leu
            20                  25                  30

Ala Glu Tyr Asp Leu Val Ile Glu Thr Tyr Gly Glu Leu Asn Ala Thr
        35                  40                  45

Gln Ser Asn Ala Val Leu Ile Cys His Ala Leu Ser Gly His His His
    50                  55                  60

Ala Ala Gly Tyr His Ser Val Asp Glu Arg Lys Pro Gly Trp Trp Asp
65                  70                  75                  80

Ser Cys Ile Gly Pro Gly Lys Pro Ile Asp Thr Arg Lys Phe Phe Val
                85                  90                  95

Val Ala Leu Asn Asn Leu Gly Gly Cys Asn Gly Ser Ser Gly Pro Ala
            100                 105                 110

Ser Ile Asn Pro Ala Thr Gly Lys Val Tyr Gly Ala Asp Phe Pro Met
        115                 120                 125

Val Thr Val Glu Asp Trp Val His Ser Gln Ala Arg Leu Ala Asp Arg
    130                 135                 140

Leu Gly Ile Arg Gln Trp Ala Ala Val Val Gly Gly Ser Leu Gly Gly
145                 150                 155                 160

Met Gln Ala Leu Gln Trp Thr Ile Ser Tyr Pro Glu Arg Val Arg His
                165                 170                 175

Cys Leu Cys Ile Ala Ser Ala Pro Lys Leu Ser Ala Gln Asn Ile Ala
            180                 185                 190

Phe Asn Glu Val Ala Arg Gln Ala Ile Leu Ser Asp Pro Glu Phe Leu
```

-continued

```
                        195                 200                 205
Gly Gly Tyr Phe Gln Glu Gln Gly Val Ile Pro Lys Arg Gly Leu Lys
    210                 215                 220

Leu Ala Arg Met Val Gly His Ile Thr Tyr Leu Ser Asp Asp Ala Met
225                 230                 235                 240

Gly Ala Lys Phe Gly Arg Val Leu Lys Thr Glu Lys Leu Asn Tyr Asp
                245                 250                 255

Leu His Ser Val Glu Phe Gln Val Glu Ser Tyr Leu Arg Tyr Gln Gly
            260                 265                 270

Glu Glu Phe Ser Thr Arg Phe Asp Ala Asn Thr Tyr Leu Leu Met Thr
        275                 280                 285

Lys Ala Leu Asp Tyr Phe Asp Pro Ala Ala Ala His Gly Asp Asp Leu
290                 295                 300

Val Arg Thr Leu Glu Gly Val Glu Ala Asp Phe Cys Leu Met Ser Phe
305                 310                 315                 320

Thr Thr Asp Trp Arg Phe Ser Pro Ala Arg Ser Arg Glu Ile Val Asp
                325                 330                 335

Ala Leu Ile Ala Ala Lys Lys Asn Val Ser Tyr Leu Glu Ile Asp Ala
            340                 345                 350

Pro Gln Gly His Asp Ala Phe Leu Met Pro Ile Pro Arg Tyr Leu Gln
        355                 360                 365

Ala Phe Ser Gly Tyr Met Asn Arg Ile Ser Val
    370                 375

<210> SEQ ID NO 4
<211> LENGTH: 1140
<212> TYPE: DNA
<213> ORGANISM: Pseudomonas aeruginosa
<220> FEATURE:
<221> NAME/KEY: misc_feature
<223> OTHER INFORMATION: metX1

<400> SEQUENCE: 4
atgcccacag tcttccccga cgactccgtc ggtctggtct cccccagac gctgcacttc      60 aacgaaccgc tcgagctgac cagcggcaag tccctggccg agtacgacct ggtgatcgaa     120
acctacggcg agctgaatgc cacgcagagc aacgcggtgc tgatctgcca cgccctctcc     180
ggccaccacc acgccgccgg ctaccacagc gtcgacgagc gcaagccggg ctggtgggac     240
agctgcatcg gtccgggcaa gccgatcgac acccgcaagt tcttcgtcgt cgccctcaac     300
aacctcggcg gttgcaacgg atccagcggc ccgccagca tcaatccggc gaccggcaag     360
gtctacggcg cggacttccc gatggttacg gtggaagact gggtgcatag ccaggcgcgc     420
ctggcagacc gcctcggcat ccgccagtgg gccgcgtgg tcggcggcag cctcggcggc     480
atgcaggcgc tgcaatggac catcagctat cccgagcgcg tccgtcactg cctgtgcatc     540
gccagcgcgc cgaagctgtc ggcgcagaac atcgccttca cgaagtcgc ccggcaggcg     600 attctttccg accctgagtt cctcggcggc tacttccagg gcagggcgt gattcccaag     660 cgcggcctca gctggcgcg gatggtcggc catatcacct acctgtccga cgacgccatg     720
ggcgccaagt tcggccgtgt actgaagacc gagaagctca actacgacct gcacagcgtc     780
gagttccagg tcgagagtta cctgcgctac cagggcgagg agttctccac ccgcttcgac     840
gccaatacct acctgctgat gaccaaggcg ctggactact cgacccgc cgccgcccac     900 ggcgacgacc tggtgcgcac cctggagggc gtcgaggcgg acttctgcct gatgtccttc     960
accaccgact ggcgtttctc gccggcccgc tcgcgggaaa tcgtcgacgc cctgatcgcg    1020
```

```
gcgaaaaaga acgtcagcta cctggagatc gacgccccgc aaggccacga cgccttcctc      1080
atgccgatcc cccggtacct gcaagccttc agcggttaca tgaaccgcat cagcgtgtga      1140
```

<210> SEQ ID NO 5
<211> LENGTH: 28
<212> TYPE: DNA
<213> ORGANISM: Artificial Sequence
<220> FEATURE:
<223> OTHER INFORMATION: Synthetic primer

<400> SEQUENCE: 5

```
ggatcccctc gttgttcacc cagcaacc                                          28
```

<210> SEQ ID NO 6
<211> LENGTH: 30
<212> TYPE: DNA
<213> ORGANISM: Artificial Sequence
<220> FEATURE:
<223> OTHER INFORMATION: Synthetic primer

<400> SEQUENCE: 6

```
ggatcccaaa gtcacaacta cttatgttag                                        30
```

<210> SEQ ID NO 7
<211> LENGTH: 33
<212> TYPE: DNA
<213> ORGANISM: Artificial Sequence
<220> FEATURE:
<223> OTHER INFORMATION: Synthetic primer

<400> SEQUENCE: 7

```
gtagataccg atattcggta cccctaccac cag                                    33
```

<210> SEQ ID NO 8
<211> LENGTH: 33
<212> TYPE: DNA
<213> ORGANISM: Artificial Sequence
<220> FEATURE:
<223> OTHER INFORMATION: Synthetic primer

<400> SEQUENCE: 8

```
ctggtggtag gggtaccgaa tatcggtatc tac                                    33
```

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9

```
tctagatgcg ctgattatct cacc                                              24
```

<210> SEQ ID NO 10
<211> LENGTH: 40
<212> TYPE: DNA
<213> ORGANISM: Artificial Sequence
<220> FEATURE:
<223> OTHER INFORMATION: Synthetic primer

<400> SEQUENCE: 10

```
actggtgggt catggttgca tatgagatca actcctgtaa                             40
```

<210> SEQ ID NO 11

```
<211> LENGTH: 40
<212> TYPE: DNA
<213> ORGANISM: Artificial Sequence
<220> FEATURE:
<223> OTHER INFORMATION: Synthetic primer

<400> SEQUENCE: 11
ttacaggagt tgatctcata tgcaaccatg acccaccagt                          40

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
tctagacctt gaagttcttg actg                                          24

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
tctagaagta gcgttgctgt acac                                          24

<210> SEQ ID NO 14
<211> LENGTH: 43
<212> TYPE: DNA
<213> ORGANISM: Artificial Sequence
<220> FEATURE:
<223> OTHER INFORMATION: Synthetic primer

<400> SEQUENCE: 14
atcaatggtc tcgatgccca tatggcattt ggaggtcctt aag                     43

<210> SEQ ID NO 15
<211> LENGTH: 43
<212> TYPE: DNA
<213> ORGANISM: Artificial Sequence
<220> FEATURE:
<223> OTHER INFORMATION: Synthetic primer

<400> SEQUENCE: 15
cttaaggacc tccaaatgcc atatgggcat cgagaccatt gat                     43

<210> SEQ ID NO 16
<211> LENGTH: 24
<212> TYPE: DNA
<213> ORGANISM: Artificial Sequence
<220> FEATURE:
<223> OTHER INFORMATION: Synthetic peptide

<400> SEQUENCE: 16
tctagatgga accgttgcaa ccac                                          24

<210> SEQ ID NO 17
<211> LENGTH: 421
<212> TYPE: PRT
<213> ORGANISM: Corynebacterium glutamicum
<220> FEATURE:
<221> NAME/KEY: MISC_FEATURE
<223> OTHER INFORMATION: lysC
```

-continued

<400> SEQUENCE: 17

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415
```

Ala Gly Thr Gly Arg
        420

<210> SEQ ID NO 18
<211> LENGTH: 1266
<212> TYPE: DNA
<213> ORGANISM: Corynebacterium glutamicum
<220> FEATURE:
<221> NAME/KEY: misc_feature
<223> OTHER INFORMATION: lysC

<400> SEQUENCE: 18

```
atggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat cttthcacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg cttthgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtcttata gtaatgatcc cggcactttg     720
attgccggct ctatggagga tattcctgtg gaagaagcag tccttaccgg tgtcgcaacc     780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca actggaccaa tgtgcttthac    1020
gacgaccagg tcggcaaagt ctccctcgtg ggtgctggac tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                                1266
```

<210> SEQ ID NO 19
<211> LENGTH: 29
<212> TYPE: DNA
<213> ORGANISM: Artificial Sequence
<220> FEATURE:
<223> OTHER INFORMATION: Synthetic primer

<400> SEQUENCE: 19

```
tcctctagag ctgcgcagtg ttgaatacg                                         29
```

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

```
<400> SEQUENCE: 20
caccgacatc atcttcacct gcc                                                  23

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
ggcaggtgaa gatgatgtcg gtg                                                  23

<210> SEQ ID NO 22
<211> LENGTH: 29
<212> TYPE: DNA
<213> ORGANISM: Artificial Sequence
<220> FEATURE:
<223> OTHER INFORMATION: Synthetic primer

<400> SEQUENCE: 22
gactctagag ttcacctcag agacgatta                                            29

<210> SEQ ID NO 23
<211> LENGTH: 421
<212> TYPE: PRT
<213> ORGANISM: Corynebacterium glutamicum
<220> FEATURE:
<221> NAME/KEY: MISC_FEATURE
<223> OTHER INFORMATION: lysC variant (T311I)

<400> SEQUENCE: 23
```

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn

```
                 210                  215                  220
Val Pro Leu Arg Val Arg Ser Ser Tyr Ser Asn Asp Pro Gly Thr Leu
225                 230                  235                  240

Ile Ala Gly Ser Met Glu Asp Ile Pro Val Glu Ala Val Leu Thr
                245                  250                  255

Gly Val Ala Thr Asp Lys Ser Glu Ala Lys Val Thr Val Leu Gly Ile
                260                  265                  270

Ser Asp Lys Pro Gly Glu Ala Ala Lys Val Phe Arg Ala Leu Ala Asp
            275                  280                  285

Ala Glu Ile Asn Ile Asp Met Val Leu Gln Asn Val Ser Ser Val Glu
        290                  295                  300

Asp Gly Thr Thr Asp Ile Ile Phe Thr Cys Pro Arg Ser Asp Gly Arg
305                 310                  315                  320

Arg Ala Met Glu Ile Leu Lys Lys Leu Gln Val Gln Gly Asn Trp Thr
                325                  330                  335

Asn Val Leu Tyr Asp Asp Gln Val Gly Lys Val Ser Leu Val Gly Ala
                340                  345                  350

Gly Met Lys Ser His Pro Gly Val Thr Ala Glu Phe Met Glu Ala Leu
                355                  360                  365

Arg Asp Val Asn Val Asn Ile Glu Leu Ile Ser Thr Ser Glu Ile Arg
    370                  375                  380

Ile Ser Val Leu Ile Arg Glu Asp Asp Leu Asp Ala Ala Ala Arg Ala
385                 390                  395                  400

Leu His Glu Gln Phe Gln Leu Gly Gly Glu Asp Glu Ala Val Val Tyr
                405                  410                  415

Ala Gly Thr Gly Arg
            420

<210> SEQ ID NO 24
<211> LENGTH: 1266
<212> TYPE: DNA
<213> ORGANISM: Corynebacterium glutamicum
<220> FEATURE:
<221> NAME/KEY: misc_feature
<223> OTHER INFORMATION: lysC variant (T311I)

<400> SEQUENCE: 24
atggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg agacaccac ggatgaactt ctagaacttg cagcggcagt gaatcccgtt      180
ccgccagctc gtgaaatgga tatgctcctg actgctggtg agcgtatttc taacgctctc     240
gtcgccatgg ctattgagtc ccttggcgca gaagcccaat cttttacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg cttttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt ggctccaag attttggtgc tgcgcagtgt tgaatacgct     660
cgtgcattca atgtgccact tcgcgtacgc tcgtcttata gtaatgatcc cggcacttg     720 attgccggct ctatggagga tattcctgtg aagaagcag tccttaccgg tgtcgcaacc     780
gacaagtccg aagccaaagt aaccgttctg ggtatttccg ataagccagg cgaggctgcg     840
```

```
aaggttttcc gtgcgttggc tgatgcagaa atcaacattg acatggttct gcagaacgtc      900
tcttctgtag aagacggcac caccgacatc atcttcacct gccctcgttc cgacggccgc      960
cgcgcgatgg agatcttgaa gaagcttcag gttcagggca actggaccaa tgtgctttac     1020
gacgaccagg tcggcaaagt ctccctcgtg gtgctggact gaagtctca cccaggtgtt     1080 accgcagagt tcatggaagc tctgcgcgat gtcaacgtga acatcgaatt gatttccacc     1140
tctgagattc gtatttccgt gctgatccgt gaagatgatc tggatgctgc tgcacgtgca     1200
ttgcatgagc agttccagct gggcggcgaa gacgaagccg tcgtttatgc aggcaccgga     1260
cgctaa                                                                 1266
```

<210> SEQ ID NO 25
<211> LENGTH: 33
<212> TYPE: DNA
<213> ORGANISM: Artificial Sequence
<220> FEATURE:
<223> OTHER INFORMATION: Sequence primer
<220> FEATURE:
<221> NAME/KEY: misc_feature
<223> OTHER INFORMATION: Forward primer for L313F

<400> SEQUENCE: 25

```
gtagataccg atatttttta cccctaccac cag                                    33
```

<210> SEQ ID NO 26
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313F

<400> SEQUENCE: 26

```
ctggtggtag gggtaaaaaa tatcggtatc tac                                    33
```

<210> SEQ ID NO 27
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313S

<400> SEQUENCE: 27

```
gtagataccg atatttctta cccctaccac cag                                    33
```

<210> SEQ ID NO 28
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313S

<400> SEQUENCE: 28

```
gtagataccg atatttctta cccctaccac cag                                    33
```

<210> SEQ ID NO 29

```
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313Y

<400> SEQUENCE: 29
gtagataccg atatttatta ccccctaccac cag                             33

<210> SEQ ID NO 30
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313Y

<400> SEQUENCE: 30
ctggtggtag gggtaataaa tatcggtatc tac                              33

<210> SEQ ID NO 31
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313C

<400> SEQUENCE: 31
gtagataccg atatttgtta ccccctaccac cag                             33

<210> SEQ ID NO 32
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313C

<400> SEQUENCE: 32
ctggtggtag gggtaacaaa tatcggtatc tac                              33

<210> SEQ ID NO 33
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313P

<400> SEQUENCE: 33
gtagataccg atattcctta ccccctaccac cag                             33

<210> SEQ ID NO 34
<211> LENGTH: 33
<212> TYPE: DNA
<213> ORGANISM: Artificial Sequence
<220> FEATURE:
```

<223> OTHER INFORMATION: Synthetic primer
<220> FEATURE:
<221> NAME/KEY: misc_feature
<223> OTHER INFORMATION: Reverse primer for L313P

<400> SEQUENCE: 34
ctggtggtag gggtaaggaa tatcggtatc tac        33

<210> SEQ ID NO 35
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313H

<400> SEQUENCE: 35
gtagataccg atattcatta cccctaccac cag        33

<210> SEQ ID NO 36
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313H

<400> SEQUENCE: 36
ctggtggtag gggtaatgaa tatcggtatc tac        33

<210> SEQ ID NO 37
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313Q

<400> SEQUENCE: 37
gtagataccg atattcaata cccctaccac cag        33

<210> SEQ ID NO 38
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313Q

<400> SEQUENCE: 38
ctggtggtag gggtattgaa tatcggtatc tac        33

<210> SEQ ID NO 39
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313I

```
<400> SEQUENCE: 39
gtagataccg atattatcta cccctaccac cag                               33

<210> SEQ ID NO 40
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313I

<400> SEQUENCE: 40
ctggtggtag gggtagataa tatcggtatc tac                              33

<210> SEQ ID NO 41
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313T

<400> SEQUENCE: 41
gtagataccg atattaccta cccctaccac cag                              33

<210> SEQ ID NO 42
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313T

<400> SEQUENCE: 42
ctggtggtag gggtaggtaa tatcggtatc tac                              33

<210> SEQ ID NO 43
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313N

<400> SEQUENCE: 43
gtagataccg atattaacta cccctaccac cag                              33

<210> SEQ ID NO 44
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313N

<400> SEQUENCE: 44
ctggtggtag gggtagttaa tatcggtatc tac                              33
```

<210> SEQ ID NO 45
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313K

<400> SEQUENCE: 45
gtagataccg atattaaata ccccctaccac cag        33

<210> SEQ ID NO 46
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313K

<400> SEQUENCE: 46
ctggtggtag gggtatttaa tatcggtatc tac        33

<210> SEQ ID NO 47
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313V

<400> SEQUENCE: 47
gtagataccg atattgttta ccccctaccac cag        33

<210> SEQ ID NO 48
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313V

<400> SEQUENCE: 48
ctggtggtag gggtaaacaa tatcggtatc tac        33

<210> SEQ ID NO 49
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313A

<400> SEQUENCE: 49
gtagataccg atattgcata ccccctaccac cag        33

<210> SEQ ID NO 50
<211> LENGTH: 33

```
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313A

<400> SEQUENCE: 50
ctggtggtag gggtatgcaa tatcggtatc tac                                33

<210> SEQ ID NO 51
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313D

<400> SEQUENCE: 51
gtagataccg atattgacta ccccctaccac cag                               33

<210> SEQ ID NO 52
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313D

<400> SEQUENCE: 52
ctggtggtag gggtagtcaa tatcggtatc tac                                33

<210> SEQ ID NO 53
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313E

<400> SEQUENCE: 53
gtagataccg atattgaata ccccctaccac cag                               33

<210> SEQ ID NO 54
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313E

<400> SEQUENCE: 54
ctggtggtag gggtattcaa tatcggtatc tac                                33

<210> SEQ ID NO 55
<211> LENGTH: 33
<212> TYPE: DNA
<213> ORGANISM: Artificial Sequence
<220> FEATURE:
<223> OTHER INFORMATION: Synthetic primer
```

```
<220> FEATURE:
<221> NAME/KEY: misc_feature
<223> OTHER INFORMATION: Forward primer for L313G

<400> SEQUENCE: 55
gtagataccg atattggata cccctaccac cag                                    33

<210> SEQ ID NO 56
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313G

<400> SEQUENCE: 56
ctggtggtag gggtatccaa tatcggtatc tac                                    33

<210> SEQ ID NO 57
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for L313W

<400> SEQUENCE: 57
gtagataccg atatttggta cccctaccac cag                                    33

<210> SEQ ID NO 58
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for L313W

<400> SEQUENCE: 58
ctggtggtag gggtaccaaa tatcggtatc tac                                    33

<210> SEQ ID NO 59
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: metX L313R

<400> SEQUENCE: 59

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
```

65                  70                  75                  80
        Tyr Cys Val Ile Cys Thr Asn Val Ile Gly Gly Cys Asn Gly Ser Thr
                        85                  90                  95

Gly Pro Gly Ser Met His Pro Asp Gly Asn Phe Trp Gly Asn Arg Phe
                    100                 105                 110

Pro Ala Thr Ser Ile Arg Asp Gln Val Asn Ala Glu Lys Gln Phe Leu
                115                 120                 125

Asp Ala Leu Gly Ile Thr Thr Val Ala Ala Val Leu Gly Gly Ser Met
            130                 135                 140

Gly Gly Ala Arg Thr Leu Glu Trp Ala Ala Met Tyr Pro Glu Thr Val
        145                 150                 155                 160

Gly Ala Ala Ala Val Leu Ala Val Ser Ala Arg Ala Ser Ala Trp Gln
                        165                 170                 175

Ile Gly Ile Gln Ser Ala Gln Ile Lys Ala Ile Glu Asn Asp His His
                    180                 185                 190

Trp His Glu Gly Asn Tyr Tyr Glu Ser Gly Cys Asn Pro Ala Thr Gly
                195                 200                 205

Leu Gly Ala Ala Arg Arg Ile Ala His Leu Thr Tyr Arg Gly Glu Leu
            210                 215                 220

Glu Ile Asp Glu Arg Phe Gly Thr Lys Ala Gln Lys Asn Glu Asn Pro
        225                 230                 235                 240

Leu Gly Pro Tyr Arg Lys Pro Asp Gln Arg Phe Ala Val Glu Ser Tyr
                        245                 250                 255

Leu Asp Tyr Gln Ala Asp Lys Leu Val Gln Arg Phe Asp Ala Gly Ser
                    260                 265                 270

Tyr Val Leu Leu Thr Asp Ala Leu Asn Arg His Asp Ile Gly Arg Asp
                275                 280                 285

Arg Gly Gly Leu Asn Lys Ala Leu Glu Ser Ile Lys Val Pro Val Leu
            290                 295                 300

Val Ala Gly Val Asp Thr Asp Ile Arg Tyr Pro Tyr His Gln Gln Glu
        305                 310                 315                 320

His Leu Ser Arg Asn Leu Gly Asn Leu Leu Ala Met Ala Lys Ile Val
                        325                 330                 335

Ser Pro Val Gly His Asp Ala Phe Leu Thr Glu Ser Arg Gln Met Asp
                    340                 345                 350

Arg Ile Val Arg Asn Phe Phe Ser Leu Ile Ser Pro Asp Glu Asp Asn
                355                 360                 365

Pro Ser Thr Tyr Ile Glu Phe Tyr Ile
            370                 375

<210> SEQ ID NO 60
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: metX L313R

<400> SEQUENCE: 60
atgcccaccc tcgcgccttc aggtcaactt gaaatccaag cgatcggtga tgtctccacc    60
gaagccggag caatcattac aaacgctgaa atcgcctatc accgctgggg tgaataccgc   120
gtagataaag aaggacgcag caatgtcgtt ctcatcgaac acgccctcac tggagattcc   180
aacgcagccg attggtgggc tgacttgctc ggtcccggca aagccatcaa cactgatatt   240

```
tactgcgtga tctgtaccaa cgtcatcggt ggttgcaacg gttccaccgg acctggctcc    300
atgcatccag atggaaattt ctggggtaat cgcttccccg ccacgtccat tcgtgatcag    360
gtaaacgccg aaaaacaatt cctcgacgca ctcggcatca ccacggtcgc cgcagtactt    420
ggtggttcca tgggtggtgc ccgcacccta gagtgggccg caatgtaccc agaaactgtt    480
ggcgcagctg ctgttcttgc agtttctgca cgcgccagcg cctggcaaat cggcattcaa    540
tccgcccaaa ttaaggcgat tgaaaacgac caccactggc acgaaggcaa ctactacgaa    600
tccggctgca acccagccac cggactcggc gccgcccgac gcatcgccca cctcacctac    660
cgtggcgaac tagaaatcga cgaacgcttc ggcaccaaag cccaaaagaa cgaaaaccca    720
ctcggtccct accgcaagcc cgaccagcgc ttcgccgtgg aatcctactt ggactaccaa    780
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatattcggt accccta cca ccagcaagaa    960
cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caacccttcg acctacatcg agttctacat ctaa         1134
```

<210> SEQ ID NO 61
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313F

<400> SEQUENCE: 61

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

```
Trp His Glu Gly Asn Tyr Tyr Glu Ser Gly Cys Asn Pro Ala Thr Gly
            195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
                275                 280                 285

Arg Gly Gly Leu Asn Lys Ala Leu Glu Ser Ile Lys Val Pro Val Leu
    290                 295                 300

Val Ala Gly Val Asp Thr Asp Ile Phe Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
                355                 360                 365

Pro Ser Thr Tyr Ile Glu Phe Tyr Ile
            370                 375

<210> SEQ ID NO 62
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313F

<400> SEQUENCE: 62
atgcccaccc tcgcgccttc aggtcaactt gaaatccaag cgatcggtga tgtctccacc        60
gaagccggag caatcattac aaacgctgaa atcgcctatc accgctgggg tgaataccgc       120
gtagataaag aaggacgcag caatgtcgtt ctcatcgaac acgccctcac tggagattcc       180
aacgcagccg attggtgggc tgacttgctc ggtcccggca agccatcaa cactgatatt       240 tactgcgtga tctgtaccaa cgtcatcggt ggttgcaacg gttccaccgg acctggctcc       300
atgcatccag atggaaattt ctggggtaat cgcttcccg ccacgtccat tcgtgatcag       360
gtaaacgccg aaaaacaatt cctcgacgca ctcggcatca ccacggtcgc cgcagtactt       420
ggtggttcca tgggtggtgc ccgcacccta gagtgggccg caatgtaccc agaaactgtt       480
ggcgcagctg ctgttcttgc agtttctgca cgcgccagcg cctggcaaat cggcattcaa       540
tccgcccaaa ttaaggcgat tgaaaacgac caccactggc acgaaggcaa ctactacgaa       600
tccggctgca acccagccac cggactcggc gccgccgac gcatcgccca cctcacctac       660
cgtggcgaac tagaaatcga cgaacgcttc ggcaccaaag cccaaaagaa cgaaaaccca       720
ctcggtccct accgcaagcc cgaccagcgc ttcgccgtgg aatcctactt ggactaccaa       780
gcagacaagc tagtacagcg tttcgacgcc ggctcctacg tcttgctcac cgacgccctc       840
aaccgccacg acattggtcg cgaccgcgga ggcctcaaca aggcactcga atccatcaaa       900
```

-continued

```
gttccagtcc ttgtcgcagg cgtagatacc gatattttt accccctacca ccagcaagaa      960
cacctctcca gaaacctggg aaatctactg gcaatggcaa aaatcgtatc ccctgtcggc     1020
cacgatgctt tcctcaccga aagccgccaa atggatcgca tcgtgaggaa cttcttcagc     1080
ctcatctccc cagacgaaga caaccccttcg acctacatcg agttctacat ctaa         1134
```

<210> SEQ ID NO 63
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313S

<400> SEQUENCE: 63

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
                20                  25                  30

Tyr His Arg Trp Gly Glu Tyr Arg Val Asp Lys Glu Gly Arg Ser Asn
            35                  40                  45

Val Val Leu Ile Glu His Ala Leu Thr Gly Asp Ser Asn Ala Ala Asp
        50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300
```

Val Ala Gly Val Asp Thr Asp Ile Ser Tyr Pro Tyr His Gln Gln Glu
305                 310                 315                 320

His Leu Ser Arg Asn Leu Gly Asn Leu Leu Ala Met Ala Lys Ile Val
            325                 330                 335

Ser Pro Val Gly His Asp Ala Phe Leu Thr Glu Ser Arg Gln Met Asp
        340                 345                 350

Arg Ile Val Arg Asn Phe Phe Ser Leu Ile Ser Pro Asp Glu Asp Asn
            355                 360                 365

Pro Ser Thr Tyr Ile Glu Phe Tyr Ile
        370                 375

<210> SEQ ID NO 64
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313S

<400> SEQUENCE: 64

```
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt     240
tactgcgtga tctgtaccaa cgtcatcggt ggttgcaacg gttccaccgg acctggctcc     300
atgcatccag atggaaattt ctggggtaat cgcttccccg ccacgtccat tcgtgatcag     360
gtaaacgccg aaaaacaatt cctcgacgca ctcggcatca ccacggtcgc cgcagtactt     420
ggtggttcca tgggtggtgc ccgcacccta gagtgggccg caatgtaccc agaaactgtt     480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgcccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
gcagacaagc tagtacagcg tttcgacgcc ggctcctacg tcttgctcac cgacgccctc     840
aaccgccacg acattggtcg cgaccgcgga ggcctcaaca aggcactcga atccatcaaa     900
gttccagtcc ttgtcgcagg cgtagatacc gatatttctt accccaccca ccagcaagaa     960
cacctctcca gaaacctggg aaatctactg gcaatggcaa aaatcgtatc ccctgtcggc    1020
cacgatgctt tcctcaccga aagccgccaa atggatcgca tcgtgaggaa cttcttcagc    1080
ctcatctccc cagacgaaga caaccccttcg acctacatcg agttctacat ctaa         1134
```

<210> SEQ ID NO 65
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313Y

<400> SEQUENCE: 65

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Ala Asp Leu Leu Gly Pro Gly Lys Ala Ile Asn Thr Asp Ile
65              70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
                100                 105                 110

Pro Ala Thr Ser Ile Arg Asp Gln Val Asn Ala Glu Lys Gln Phe Leu
            115                 120                 125

Asp Ala Leu Gly Ile Thr Thr Val Ala Ala Val Leu Gly Gly Ser Met
        130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Tyr Tyr Pro Tyr His Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 66
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313Y

<400> SEQUENCE: 66

```
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt      240
tactgcgtga tctgtaccaa cgtcatcggt ggttgcaacg gttccaccgg acctggctcc     300
atgcatccag atggaaattt ctggggtaat cgcttccccg ccacgtccat tcgtgatcag     360
gtaaacgccg aaaaacaatt cctcgacgca ctcggcatca ccacggtcgc cgcagtactt    420
ggtggttcca tgggtggtgc ccgcacccta gagtgggccg caatgtaccc agaaactgtt    480
ggcgcagctg ctgttcttgc agtttctgca cgcgccagcg cctggcaaat cggcattcaa    540
tccgcccaaa ttaaggcgat tgaaaacgac caccactggc acgaaggcaa ctactacgaa    600
tccggctgca acccagccac cggactcggc gccgcccgac gcatcgccca cctcacctac    660
cgtggcgaac tagaaatcga cgaacgcttc ggcaccaaag cccaaaagaa cgaaaaccca    720
ctcggtccct accgcaagcc cgaccagcgc ttcgccgtgg aatcctactt ggactaccaa    780
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatatttatt accccctacca ccagcaagaa  960
cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caaccctttcg acctacatcg agttctacat ctaa        1134
```

<210> SEQ ID NO 67
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313C

<400> SEQUENCE: 67

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
```

```
            115                 120                 125
Asp Ala Leu Gly Ile Thr Thr Val Ala Ala Val Leu Gly Gly Ser Met
    130                 135                 140
Gly Gly Ala Arg Thr Leu Glu Trp Ala Ala Met Tyr Pro Glu Thr Val
145                 150                 155                 160
Gly Ala Ala Ala Val Leu Ala Val Ser Ala Arg Ala Ser Ala Trp Gln
                165                 170                 175
Ile Gly Ile Gln Ser Ala Gln Ile Lys Ala Ile Glu Asn Asp His His
            180                 185                 190
Trp His Glu Gly Asn Tyr Tyr Glu Ser Gly Cys Asn Pro Ala Thr Gly
        195                 200                 205
Leu Gly Ala Ala Arg Arg Ile Ala His Leu Thr Tyr Arg Gly Glu Leu
    210                 215                 220
Glu Ile Asp Glu Arg Phe Gly Thr Lys Ala Gln Lys Asn Glu Asn Pro
225                 230                 235                 240
Leu Gly Pro Tyr Arg Lys Pro Asp Gln Arg Phe Ala Val Glu Ser Tyr
                245                 250                 255
Leu Asp Tyr Gln Ala Asp Lys Leu Val Gln Arg Phe Asp Ala Gly Ser
            260                 265                 270
Tyr Val Leu Leu Thr Asp Ala Leu Asn Arg His Asp Ile Gly Arg Asp
        275                 280                 285
Arg Gly Gly Leu Asn Lys Ala Leu Glu Ser Ile Lys Val Pro Val Leu
    290                 295                 300
Val Ala Gly Val Asp Thr Asp Ile Cys Tyr Pro Tyr His Gln Gln Glu
305                 310                 315                 320
His Leu Ser Arg Asn Leu Gly Asn Leu Leu Ala Met Ala Lys Ile Val
                325                 330                 335
Ser Pro Val Gly His Asp Ala Phe Leu Thr Glu Ser Arg Gln Met Asp
            340                 345                 350
Arg Ile Val Arg Asn Phe Phe Ser Leu Ile Ser Pro Asp Glu Asp Asn
        355                 360                 365
Pro Ser Thr Tyr Ile Glu Phe Tyr Ile
    370                 375

<210> SEQ ID NO 68
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313C

<400> SEQUENCE: 68
atgcccaccc tcgcgccttc aggtcaactt gaaatccaag cgatcggtga tgtctccacc    60
gaagccggag caatcattac aaacgctgaa atcgcctatc accgctgggg tgaataccgc   120
gtagataaag aaggacgcag caatgtcgtt ctcatcgaac acgccctcac tggagattcc   180
aacgcagccg attggtgggc tgacttgctc ggtcccggca agccatcaa cactgatatt   240 tactgcgtga tctgtaccaa cgtcatcggt ggttgcaacg ttccaccgg acctggctcc   300 atgcatccag atggaaattt ctggggtaat cgcttccccg ccacgtccat tcgtgatcag   360
gtaaacgccg aaaacaatt cctcgacgca ctcggcatca ccacggtcgc cgcagtactt   420
ggtggttcca tgggtggtgc ccgcacccta gagtgggccg caatgtaccc agaaactgtt   480
```

-continued

```
ggcgcagctg ctgttcttgc agtttctgca cgcgccagcg cctggcaaat cggcattcaa      540
tccgcccaaa ttaaggcgat tgaaaacgac caccactggc acgaaggcaa ctactacgaa      600
tccggctgca acccagccac cggactcggc gccgcccgac gcatcgccca cctcacctac      660
cgtggcgaac tagaaatcga cgaacgcttc ggcaccaaag cccaaaagaa cgaaaaccca      720
ctcggtccct accgcaagcc cgaccagcgc ttcgccgtgg aatcctactt ggactaccaa      780
gcagacaagc tagtacagcg tttcgacgcc ggctcctacg tcttgctcac cgacgccctc      840
aaccgccacg acattggtcg cgaccgcgga ggcctcaaca aggcactcga atccatcaaa      900
gttccagtcc ttgtcgcagg cgtagatacc gatatttgtt accccctacca ccagcaagaa      960 cacctctcca gaaacctggg aaatctactg gcaatggcaa aaatcgtatc ccctgtcggc     1020
cacgatgctt tcctcaccga aagccgccaa atggatcgca tcgtgaggaa cttcttcagc     1080
ctcatctccc cagacgaaga caaccctccg acctacatcg agttctacat ctaa           1134
```

<210> SEQ ID NO 69
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313P

<400> SEQUENCE: 69

```
Met Pro Thr Leu Ala Pro Ser Gly Gln Leu Glu Ile Gln Ala Ile Gly
1               5                  10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240
```

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Pro Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 70
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313P

<400> SEQUENCE: 70

```
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt     240 tactgcgtga tctgtaccaa cgtcatcggt ggttgcaacg gttccaccgg acctggctcc     300
atgcatccag atggaaattt ctggggtaat cgcttccccg ccacgtccat tcgtgatcag     360
gtaaacgccg aaaaacaatt cctcgacgca ctcggcatca ccacggtcgc cgcagtactt     420
ggtggttcca tgggtggtgc ccgcacccta gagtgggccg caatgtaccc agaaactgtt     480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgcccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
gcagacaagc tagtacagcg tttcgacgcc ggctcctacg tcttgctcac cgacgccctc     840
aaccgccacg acattggtcg cgaccgcgga ggcctcaaca aggcactcga atccatcaaa     900
gttccagtcc ttgtcgcagg cgtagatacc gatattcctt accctaccca ccagcaagaa     960
cacctctcca gaaacctggg aaatctactg gcaatggcaa aaatcgtatc cctgtcggc    1020 cacgatgctt tcctcaccga aagccgccaa atggatcgca tcgtgaggaa cttcttcagc    1080
ctcatctccc cagacgaaga caacccttcg acctacatcg agttctacat ctaa          1134
```

<210> SEQ ID NO 71
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313H

<400> SEQUENCE: 71

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile His Tyr Pro Tyr His Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350
```

Arg Ile Val Arg Asn Phe Phe Ser Leu Ile Ser Pro Asp Glu Asp Asn
            355                 360                 365

Pro Ser Thr Tyr Ile Glu Phe Tyr Ile
        370                 375

<210> SEQ ID NO 72
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313H

<400> SEQUENCE: 72

| | | | | | |
|---|---|---|---|---|---|
| atgcccaccc | tcgcgccttc | aggtcaactt | gaaatccaag | cgatcggtga | tgtctccacc | 60 |
| gaagccggag | caatcattac | aaacgctgaa | atcgcctatc | accgctgggg | tgaataccgc | 120 |
| gtagataaag | aaggacgcag | caatgtcgtt | ctcatcgaac | acgccctcac | tggagattcc | 180 |
| aacgcagccg | attggtgggc | tgacttgctc | ggtcccggca | agccatcaa | cactgatatt | 240 |
| tactgcgtga | tctgtaccaa | cgtcatcggt | ggttgcaacg | gttccaccgg | acctggctcc | 300 |
| atgcatccag | atggaaattt | ctggggtaat | cgcttccccg | ccacgtccat | tcgtgatcag | 360 |
| gtaaacgccg | aaaaacaatt | cctcgacgca | ctcggcatca | ccacggtcgc | cgcagtactt | 420 |
| ggtggttcca | tgggtggtgc | ccgcacccta | gagtgggccg | caatgtaccc | agaaactgtt | 480 |
| ggcgcagctg | ctgttcttgc | agtttctgca | cgcgccagcg | cctggcaaat | cggcattcaa | 540 |
| tccgcccaaa | ttaaggcgat | tgaaaacgac | caccactggc | acgaaggcaa | ctactacgaa | 600 |
| tccggctgca | acccagccac | cggactcggc | gccgcccgac | gcatcgccca | cctcacctac | 660 |
| cgtggcgaac | tagaaatcga | cgaacgcttc | ggcaccaaag | cccaaaagaa | cgaaaaccca | 720 |
| ctcggtccct | accgcaagcc | cgaccagcgc | ttcgccgtgg | aatcctactt | ggactaccaa | 780 |
| gcagacaagc | tagtacagcg | tttcgacgcc | ggctcctacg | tcttgctcac | cgacgccctc | 840 |
| aaccgccacg | acattggtcg | cgaccgcgga | ggcctcaaca | aggcactcga | atccatcaaa | 900 |
| gttccagtcc | ttgtcgcagg | cgtagatacc | gatattcatt | accctacca | ccagcaagaa | 960 |
| cacctctcca | gaaacctggg | aaatctactg | gcaatggcaa | aaatcgtatc | ccctgtcggc | 1020 |
| cacgatgctt | tcctcaccga | aagccgccaa | atggatcgca | tcgtgaggaa | cttcttcagc | 1080 |
| ctcatctccc | cagacgaaga | caaccccttcg | acctacatcg | agttctacat | ctaa | 1134 |

<210> SEQ ID NO 73
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313Q

<400> SEQUENCE: 73

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

```
Val Val Leu Ile Glu His Ala Leu Thr Gly Asp Ser Asn Ala Ala Asp
         50                  55                  60

Trp Trp Ala Asp Leu Leu Gly Pro Gly Lys Ala Ile Asn Thr Asp Ile
 65                  70                  75                  80

Tyr Cys Val Ile Cys Thr Asn Val Ile Gly Gly Cys Asn Gly Ser Thr
                     85                  90                  95

Gly Pro Gly Ser Met His Pro Asp Gly Asn Phe Trp Gly Asn Arg Phe
                100                 105                 110

Pro Ala Thr Ser Ile Arg Asp Gln Val Asn Ala Glu Lys Gln Phe Leu
                115                 120                 125

Asp Ala Leu Gly Ile Thr Thr Val Ala Ala Val Leu Gly Gly Ser Met
130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
                180                 185                 190

Trp His Glu Gly Asn Tyr Tyr Glu Ser Gly Cys Asn Pro Ala Thr Gly
         195                 200                 205

Leu Gly Ala Ala Arg Arg Ile Ala His Leu Thr Tyr Arg Gly Glu Leu
210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
                260                 265                 270

Tyr Val Leu Leu Thr Asp Ala Leu Asn Arg His Asp Ile Gly Arg Asp
                275                 280                 285

Arg Gly Gly Leu Asn Lys Ala Leu Glu Ser Ile Lys Val Pro Val Leu
                290                 295                 300

Val Ala Gly Val Asp Thr Asp Ile Gln Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
                340                 345                 350

Arg Ile Val Arg Asn Phe Phe Ser Leu Ile Ser Pro Asp Glu Asp Asn
                355                 360                 365

Pro Ser Thr Tyr Ile Glu Phe Tyr Ile
                370                 375

<210> SEQ ID NO 74
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313Q

<400> SEQUENCE: 74
atgcccaccc tcgcgccttc aggtcaactt gaaatccaag cgatcggtga tgtctccacc        60
gaagccggag caatcattac aaacgctgaa atcgcctatc accgctgggg tgaataccgc       120
```

```
gtagataaag aaggacgcag caatgtcgtt ctcatcgaac acgccctcac tggagattcc    180
aacgcagccg attggtgggc tgacttgctc ggtcccggca aagccatcaa cactgatatt    240
tactgcgtga tctgtaccaa cgtcatcggt ggttgcaacg gttccaccgg acctggctcc    300
atgcatccag atggaaattt ctggggtaat cgcttccccg ccacgtccat tcgtgatcag    360
gtaaacgccg aaaaacaatt cctcgacgca ctcggcatca ccacggtcgc cgcagtactt    420
ggtggttcca tgggtggtgc ccgcacccta gagtgggccg caatgtaccc agaaactgtt    480
ggcgcagctg ctgttcttgc agtttctgca cgcgccagcg cctggcaaat cggcattcaa    540
tccgcccaaa ttaaggcgat tgaaaacgac caccactggc acgaaggcaa ctactacgaa    600
tccggctgca acccagccac cggactcggc gccgcccgac gcatcgccca cctcacctac    660
cgtggcgaac tagaaatcga cgaacgcttc ggcaccaaag cccaaaagaa cgaaaaccca    720
ctcggtccct accgcaagcc cgaccagcgc ttcgccgtgg aatcctactt ggactaccaa    780
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatattcaat accccaccac ccagcaagaa    960
cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caaccctcg acctacatcg agttctacat ctaa         1134
```

<210> SEQ ID NO 75
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313I

<400> SEQUENCE: 75

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
                20                  25                  30

Tyr His Arg Trp Gly Glu Tyr Arg Val Asp Lys Glu Gly Arg Ser Asn
            35                  40                  45

Val Val Leu Ile Glu His Ala Leu Thr Gly Asp Ser Asn Ala Ala Asp
        50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
```

```
            165                 170                 175
Ile Gly Ile Gln Ser Ala Gln Ile Lys Ala Ile Glu Asn Asp His His
        180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
        210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
                260                 265                 270

Tyr Val Leu Leu Thr Asp Ala Leu Asn Arg His Asp Ile Gly Arg Asp
                275                 280                 285

Arg Gly Gly Leu Asn Lys Ala Leu Glu Ser Ile Lys Val Pro Val Leu
        290                 295                 300

Val Ala Gly Val Asp Thr Asp Ile Ile Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
                340                 345                 350

Arg Ile Val Arg Asn Phe Phe Ser Leu Ile Ser Pro Asp Glu Asp Asn
                355                 360                 365

Pro Ser Thr Tyr Ile Glu Phe Tyr Ile
                370                 375

<210> SEQ ID NO 76
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313I

<400> SEQUENCE: 76
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt     240 tactgcgtga tctgtaccaa cgtcatcggt ggttgcaacg gttccaccgg acctggctcc     300
atgcatccag atgaaattt ctggggtaat cgcttccccg ccacgtccat tgtgatcag      360 gtaaacgccg aaaaacaatt cctcgacgca ctcggcatca ccacgttgcc cgcagtactt     420
ggtggttcca tgggtggtgc ccgcacccta gagtgggccg caatgtaccc agaaactgtt     480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgcccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
```

```
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatattatct acccctacca ccagcaagaa    960
cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caaccctttcg acctacatcg agttctacat ctaa        1134
```

<210> SEQ ID NO 77
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313T

<400> SEQUENCE: 77

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285
```

Arg Gly Gly Leu Asn Lys Ala Leu Glu Ser Ile Lys Val Pro Val Leu
            290                 295                 300

Val Ala Gly Val Asp Thr Asp Ile Thr Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 78
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313T

<400> SEQUENCE: 78

| | | | | | |
|---|---|---|---|---|---|
| atgcccaccc | tcgcgccttc | aggtcaactt | gaaatccaag | cgatcggtga | tgtctccacc | 60 |
| gaagccggag | caatcattac | aaacgctgaa | atcgcctatc | accgctgggg | tgaataccgc | 120 |
| gtagataaag | aaggacgcag | caatgtcgtt | ctcatcgaac | acgccctcac | tggagattcc | 180 |
| aacgcagccg | attggtgggc | tgacttgctc | ggtcccggca | agccatcaa | cactgatatt | 240 |
| tactgcgtga | tctgtaccaa | cgtcatcggt | ggttgcaacg | gttccaccgg | acctggctcc | 300 |
| atgcatccag | atggaaattt | ctggggtaat | cgcttccccg | ccacgtccat | tcgtgatcag | 360 |
| gtaaacgccg | aaaaacaatt | cctcgacgca | ctcggcatca | ccacggtcgc | cgcagtactt | 420 |
| ggtggttcca | tgggtggtgc | ccgcacccta | gagtgggccg | caatgtaccc | agaaactgtt | 480 |
| ggcgcagctg | ctgttcttgc | agtttctgca | cgcgccagcg | cctggcaaat | cggcattcaa | 540 |
| tccgcccaaa | ttaaggcgat | tgaaaacgac | caccactggc | acgaaggcaa | ctactacgaa | 600 |
| tccggctgca | acccagccac | cggactcggc | gccgccgac | gcatcgccca | cctcacctac | 660 |
| cgtggcgaac | tagaaatcga | cgaacgcttc | ggcaccaaag | cccaaaagaa | cgaaaaccca | 720 |
| ctcggtccct | accgcaagcc | cgaccagcgc | ttcgccgtgg | aatcctactt | ggactaccaa | 780 |
| gcagacaagc | tagtacagcg | tttcgacgcc | ggctcctacg | tcttgctcac | cgacgccctc | 840 |
| aaccgccacg | acattggtcg | cgaccgcgga | ggcctcaaca | aggcactcga | atccatcaaa | 900 |
| gttccagtcc | ttgtcgcagg | cgtagatacc | gatattacct | accctacca | ccagcaagaa | 960 |
| cacctctcca | gaaacctggg | aaatctactg | gcaatggcaa | aaatcgtatc | cctgtcggc | 1020 |
| cacgatgctt | tcctcaccga | aagccgccaa | atggatcgca | tcgtgaggaa | cttcttcagc | 1080 |
| ctcatctccc | cagacgaaga | caaccccttcg | acctacatcg | agttctacat | ctaa | 1134 |

<210> SEQ ID NO 79
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

<223> OTHER INFORMATION: 313N

<400> SEQUENCE: 79

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Asn Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 80
<211> LENGTH: 1134

```
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313N

<400> SEQUENCE: 80
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt      240
tactgcgtga tctgtaccaa cgtcatcggt ggttgcaacg gttccaccgg acctggctcc     300
atgcatccag atggaaattt ctggggtaat cgcttccccg ccacgtccat tcgtgatcag     360
gtaaacgccg aaaaacaatt cctcgacgca ctcggcatca ccacggtcgc cgcagtactt     420
ggtggttcca tgggtggtgc ccgcaccta gagtgggccg caatgtaccc agaaactgtt      480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgcccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
gcagacaagc tagtacagcg tttcgacgcc ggctcctacg tcttgctcac cgacgccctc     840
aaccgccacg acattggtcg cgaccgcgga ggcctcaaca aggcactcga atccatcaaa     900
gttccagtcc ttgtcgcagg cgtagatacc gatattaact accccaccaa ccagcaagaa     960
cacctctcca gaaacctggg aaatctactg caatggcaa aaatcgtatc cctgtcggc     1020
cacgatgctt tcctcaccga aagccgccaa atggatcgca tcgtgaggaa cttcttcagc     1080
ctcatctccc cagacgaaga caacccttcg acctacatcg agttctacat ctaa          1134

<210> SEQ ID NO 81
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313K

<400> SEQUENCE: 81

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95
```

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Lys Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 82
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313K

<400> SEQUENCE: 82
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt      240 tactgcgtga tctgtaccaa cgtcatcggt ggttgcaacg gttccaccgg acctggctcc     300
atgcatccag atggaaattt ctggggtaat cgcttcccg ccacgtccat tcgtgatcag     360

```
gtaaacgccg aaaaacaatt cctcgacgca ctcggcatca ccacggtcgc cgcagtactt    420
ggtggttcca tgggtggtgc ccgcacccta gagtgggccg caatgtaccc agaaactgtt    480
ggcgcagctg ctgttcttgc agtttctgca cgcgccagcg cctggcaaat cggcattcaa    540
tccgcccaaa ttaaggcgat tgaaaacgac caccactggc acgaaggcaa ctactacgaa    600
tccggctgca acccagccac cggactcggc gccgcccgac gcatcgccca cctcacctac    660
cgtggcgaac tagaaatcga cgaacgcttc ggcaccaaag cccaaaagaa cgaaaaccca    720
ctcggtccct accgcaagcc cgaccagcgc ttcgccgtgg aatcctactt ggactaccaa    780
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatattcatt accctacca ccagcaagaa    960 cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caaccccttcg acctacatcg agttctacat ctaa         1134
```

<210> SEQ ID NO 83
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313V

<400> SEQUENCE: 83

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
                20                  25                  30

Tyr His Arg Trp Gly Glu Tyr Arg Val Asp Lys Glu Gly Arg Ser Asn
            35                  40                  45

Val Val Leu Ile Glu His Ala Leu Thr Gly Asp Ser Asn Ala Ala Asp
        50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
```

```
         210                 215                 220
Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
            245                 250                 255

Leu Asp Tyr Gln Ala Asp Lys Leu Val Gln Arg Phe Asp Ala Gly Ser
                260                 265                 270

Tyr Val Leu Leu Thr Asp Ala Leu Asn Arg His Asp Ile Gly Arg Asp
            275                 280                 285

Arg Gly Gly Leu Asn Lys Ala Leu Glu Ser Ile Lys Val Pro Val Leu
        290                 295                 300

Val Ala Gly Val Asp Thr Asp Ile Val Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
                340                 345                 350

Arg Ile Val Arg Asn Phe Phe Ser Leu Ile Ser Pro Asp Glu Asp Asn
            355                 360                 365

Pro Ser Thr Tyr Ile Glu Phe Tyr Ile
        370                 375

<210> SEQ ID NO 84
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313V

<400> SEQUENCE: 84
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt      240 tactgcgtga tctgtaccaa cgtcatcggt ggttgcaacg gttccaccgg acctggctcc     300
atgcatccag atggaaattt ctggggtaat cgcttccccg ccacgtccat tcgtgatcag     360
gtaaacgccg aaaaacaatt cctcgacgca ctcggcatca ccacggtcgc cgcagtactt     420
ggtggttcca tgggtggtgc ccgcacccta gagtgggccg caatgtaccc agaaactgtt     480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
gcagacaagc tagtacagcg tttcgacgcc ggctcctacg tcttgctcac cgacgccctc     840
aaccgccacg acattggtcg cgaccgcgga ggcctcaaca aggcactcga atccatcaaa     900
gttccagtcc ttgtcgcagg cgtagatacc gatattgttt accccctacca ccagcaagaa     960 cacctctcca gaaacctggg aaatctactg gcaatggcaa aaatcgtatc ccctgtcggc    1020
```
cacgatgctt tcctcaccga aagccgccaa atggatcgca tcgtgaggaa cttcttcagc    1080
ctcatctccc cagacgaaga caaccctttcg acctacatcg agttctacat ctaa         1134

<210> SEQ ID NO 85
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313A

<400> SEQUENCE: 85

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Ala Tyr Pro Tyr His Gln Gln Glu
305                 310                 315                 320

His Leu Ser Arg Asn Leu Gly Asn Leu Leu Ala Met Ala Lys Ile Val
                325                 330                 335
```

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 86
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313A

<400> SEQUENCE: 86
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt      240 tactgcgtga tctgtaccaa cgtcatcggt ggttgcaacg ttccaccgg acctggctcc      300 atgcatccag atggaaattt ctggggtaat cgcttccccg ccacgtccat tcgtgatcag     360
gtaaacgccg aaaaacaatt cctcgacgca ctcggcatca ccacggtcgc cgcagtactt     420
ggtggttcca tgggtggtgc ccgcaccta gagtgggccg caatgtaccc agaaactgtt     480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgcccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
gcagacaagc tagtacagcg tttcgacgcc ggctcctacg tcttgctcac cgacgccctc     840
aaccgccacg acattggtcg cgaccgcgga ggcctcaaca aggcactcga atccatcaaa     900
gttccagtcc ttgtcgcagg cgtagatacc gatattgcat ccctacca ccagcaagaa      960 cacctctcca gaaacctggg aaatctactg gcaatggcaa aaatcgtatc cctgtcggc    1020 cacgatgctt tcctcaccga aagccgccaa atggatcgca tcgtgaggaa cttcttcagc    1080
ctcatctccc cagacgaaga caaccttcg acctacatcg agttctacat ctaa          1134

<210> SEQ ID NO 87
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313D

<400> SEQUENCE: 87

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

```
Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
 50                  55                  60

Trp Trp Ala Asp Leu Leu Gly Pro Gly Lys Ala Ile Asn Thr Asp Ile
 65                  70                  75                  80

Tyr Cys Val Ile Cys Thr Asn Val Ile Gly Cys Asn Gly Ser Thr
                 85                  90                  95

Gly Pro Gly Ser Met His Pro Asp Gly Asn Phe Trp Gly Asn Arg Phe
                100                 105                 110

Pro Ala Thr Ser Ile Arg Asp Gln Val Asn Ala Glu Lys Gln Phe Leu
                115                 120                 125

Asp Ala Leu Gly Ile Thr Thr Val Ala Ala Val Leu Gly Gly Ser Met
        130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
                180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
        210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
                260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
        290                 295                 300

Val Ala Gly Val Asp Thr Asp Ile Asp Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
                340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
        370                 375

<210> SEQ ID NO 88
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313D

<400> SEQUENCE: 88
```

-continued

```
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt      240
tactgcgtga tctgtaccaa cgtcatcggt ggttgcaacg gttccaccgg acctggctcc     300
atgcatccag atggaaattt ctggggtaat cgcttccccg ccacgtccat tcgtgatcag     360
gtaaacgccg aaaaacaatt cctcgacgca ctcggcatca ccacggtcgc cgcagtactt     420
ggtggttcca tgggtggtgc ccgcacccta gagtgggccg caatgtaccc agaaactgtt     480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgcccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
gcagacaagc tagtacagcg tttcgacgcc ggctcctacg tcttgctcac cgacgccctc     840
aaccgccacg acattggtcg cgaccgcgga ggcctcaaca aggcactcga atccatcaaa     900
gttccagtcc ttgtcgcagg cgtagatacc gatattgact accccacca ccagcaagaa      960
cacctctcca gaaacctggg aaatctactg gcaatggcaa aaatcgtatc ccctgtcggc    1020
cacgatgctt tcctcaccga aagccgccaa atggatcgca tcgtgaggaa cttcttcagc    1080
ctcatctccc cagacgaaga caaccttcg acctacatcg agttctacat ctaa          1134
```

<210> SEQ ID NO 89
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313E

<400> SEQUENCE: 89

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
                20                  25                  30

Tyr His Arg Trp Gly Glu Tyr Arg Val Asp Lys Glu Gly Arg Ser Asn
            35                  40                  45

Val Val Leu Ile Glu His Ala Leu Thr Gly Asp Ser Asn Ala Ala Asp
        50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
            165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
            245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Glu Tyr Pro Tyr His Gln Gln Glu
305                 310                 315                 320

His Leu Ser Arg Asn Leu Gly Asn Leu Leu Ala Met Ala Lys Ile Val
            325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
        370                 375

<210> SEQ ID NO 90
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313E

<400> SEQUENCE: 90
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt     240 tactgcgtga tctgtaccaa cgtcatcggt ggttgcaacg gttccaccgg acctggctcc     300
atgcatccag atggaaattt ctggggtaat cgcttccccg ccacgtccat tgtgatcag      360 gtaaacgccg aaaacaatt cctcgacgca ctcggcatca ccacggtcgc cgcagtactt     420
ggtggttcca tgggtggtgc ccgcacccta gagtgggccg caatgtaccc agaaactgtt     480
ggcgcagctg ctgttcttgc agtttctgca cgcgccagcg cctggcaaat cggcattcaa     540
tccgcccaaa ttaaggcgat tgaaaacgac caccactggc acgaaggcaa ctactacgaa     600
tccggctgca acccagccac cggactcggc gccgcccgac gcatcgccca cctcacctac     660

| cgtggcgaac tagaaatcga cgaacgcttc ggcaccaaag cccaaaagaa cgaaaaccca | 720 |
| ctcggtccct accgcaagcc cgaccagcgc ttcgccgtgg aatcctactt ggactaccaa | 780 |
| gcagacaagc tagtacagcg tttcgacgcc ggctcctacg tcttgctcac cgacgccctc | 840 |
| aaccgccacg acattggtcg cgaccgcgga ggcctcaaca aggcactcga atccatcaaa | 900 |
| gttccagtcc ttgtcgcagg cgtagatacc gatattgaat accccctacca ccagcaagaa | 960 |
| cacctctcca gaaacctggg aaatctactg gcaatggcaa aaatcgtatc ccctgtcggc | 1020 |
| cacgatgctt tcctcaccga aagccgccaa atggatcgca tcgtgaggaa cttcttcagc | 1080 |
| ctcatctccc cagacgaaga caaccctttcg acctacatcg agttctacat ctaa | 1134 |

<210> SEQ ID NO 91
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: 313G

<400> SEQUENCE: 91

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
```

```
            260                 265                 270
Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Gly Tyr Pro Tyr His Gln Gln Glu
305                 310                 315                 320

His Leu Ser Arg Asn Leu Gly Asn Leu Leu Ala Met Ala Lys Ile Val
            325                 330                 335

Ser Pro Val Gly His Asp Ala Phe Leu Thr Glu Ser Arg Gln Met Asp
        340                 345                 350

Arg Ile Val Arg Asn Phe Phe Ser Leu Ile Ser Pro Asp Glu Asp Asn
    355                 360                 365

Pro Ser Thr Tyr Ile Glu Phe Tyr Ile
    370                 375

<210> SEQ ID NO 92
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313G

<400> SEQUENCE: 92
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180
aacgcagccg attggtgggc tgacttgctc ggtcccggca agccatcaa cactgatatt      240 tactgcgtga tctgtaccaa cgtcatcggt ggttgcaacg gttccaccgg acctggctcc     300
atgcatccag atggaaattt ctggggtaat cgcttccccg ccacgtccat tcgtgatcag     360
gtaaacgccg aaaaacaatt cctcgacgca ctcggcatca ccacggtcgc cgcagtactt     420
ggtggttcca tgggtggtgc ccgcacccta gagtgggccg caatgtaccc agaaactgtt     480
ggcgcagctc tgttcttgc agtttctgca cgcgccagcg cctggcaaat cggcattcaa      540
tccgcccaaa ttaaggcgat tgaaaacgac caccactggc acgaaggcaa ctactacgaa     600
tccggctgca acccagccac cggactcggc gccgcccgac gcatcgccca cctcacctac     660
cgtggcgaac tagaaatcga cgaacgcttc ggcaccaaag cccaaaagaa cgaaaaccca     720
ctcggtccct accgcaagcc cgaccagcgc ttcgccgtgg aatcctactt ggactaccaa     780
gcagacaagc tagtacagcg tttcgacgcc ggctcctacg tcttgctcac cgacgccctc     840
aaccgccacg acattggtcg cgaccgcgga ggcctcaaca aggcactcga atccatcaaa     900
gttccagtcc ttgtcgcagg cgtagatacc gatattggat accctacca ccagcaagaa      960 cacctctcca gaaacctggg aaatctactg gcaatggcaa aaatcgtatc ccctgtcggc    1020
cacgatgctt tcctcaccga aagccgccaa atggatcgca tcgtgaggaa cttcttcagc    1080
ctcatctccc cagacgaaga caacccttcg acctacatcg agttctacat ctaa          1134

<210> SEQ ID NO 93
<211> LENGTH: 377
<212> TYPE: PRT
<213> ORGANISM: Artificial Sequence
```

<220> FEATURE:
<223> OTHER INFORMATION: Synthetic peptide
<220> FEATURE:
<221> NAME/KEY: MISC_FEATURE
<223> OTHER INFORMATION: 313W

<400> SEQUENCE: 93

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Trp Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 94
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: 313W

<400> SEQUENCE: 94

```
atgcccaccc tcgcgccttc aggtcaactt gaaatccaag cgatcggtga tgtctccacc        60
gaagccggag caatcattac aaacgctgaa atcgcctatc accgctgggg tgaataccgc       120
gtagataaag aaggacgcag caatgtcgtt ctcatcgaac acgccctcac tggagattcc       180
aacgcagccg attggtgggc tgacttgctc ggtcccggca aagccatcaa cactgatatt       240
tactgcgtga tctgtaccaa cgtcatcggt ggttgcaacg gttccaccgg acctggctcc       300
atgcatccag atggaaattt ctggggtaat cgcttccccg ccacgtccat tcgtgatcag       360
gtaaacgccg aaaaacaatt cctcgacgca ctcggcatca ccacggtcgc cgcagtactt       420
ggtggttcca tgggtggtgc ccgcacccta gagtgggccg caatgtaccc agaaactgtt       480
ggcgcagctg ctgttcttgc agtttctgca cgcgccagcg cctggcaaat cggcattcaa       540
tccgcccaaa ttaaggcgat tgaaaacgac caccactggc acgaaggcaa ctactacgaa       600
tccggctgca acccagccac cggactcggc gccgcccgac gcatcgccca cctcacctac       660
cgtggcgaac tagaaatcga cgaacgcttc ggcaccaaag cccaaaagaa cgaaaaccca       720
ctcggtccct accgcaagcc cgaccagcgc ttcgccgtgg aatcctactt ggactaccaa       780
gcagacaagc tagtacagcg tttcgacgcc ggctcctacg tcttgctcac cgacgccctc       840
aaccgccacg acattggtcg cgaccgcgga ggcctcaaca aggcactcga atccatcaaa       900
gttccagtcc ttgtcgcagg cgtagatacc gatatttggt accectacca ccagcaagaa       960 cacctctcca gaaacctggg aaatctactg gcaatggcaa aaatcgtatc ccctgtcggc      1020
cacgatgctt tcctcaccga aagccgccaa atggatcgca tcgtgaggaa cttcttcagc      1080
ctcatctccc cagacgaaga caaccettcg acctacatcg agttctacat ctaa            1134
```

The invention claimed is:

1. A polypeptide having O-succinyl homoserine transferase activity, the polypeptide comprising substitution of leucine at the position corresponding to amino acid 313 of SEQ ID NO: 1 with arginine, cysteine, isoleucine, or lysine, wherein the amino acid sequence of the polypeptide has at least 80% sequence identity to the amino acid sequence of SEQ ID NO: 1.

2. The polypeptide having O-succinyl homoserine transferase activity of claim 1, wherein the polypeptide comprises an amino acid sequence selected from the group consisting of SEQ ID NO: 59, SEQ ID NO: 67, SEQ ID NO: 75, and SEQ ID NO: 81.

3. A polynucleotide comprising a nucleotide sequence encoding the polypeptide having O-succinyl homoserine transferase activity of claim 1.

4. The polynucleotide of claim 3, wherein the nucleotide sequence is selected from the group consisting of SEQ ID NO: 60, SEQ ID NO: 68, SEQ ID NO: 76, and SEQ ID NO: 82.

5. An O-succinyl homoserine-producing microorganism of the genus *Corynebacterium*, wherein the microorganism comprises the polypeptide having O-succinyl homoserine transferase activity of claim 1.

6. The O-succinyl homoserine-producing microorganism of claim 5, wherein the microorganism overexpresesses an aspartokinase.

7. The O-succinyl homoserine-producing microorganism of claim 5, wherein the microorganism is *Corynebacterium glutamicum*.

8. The O-succinyl homoserine-producing microorganism of claim 5, wherein one or more genes encoding cystathionine synthase, O-acetyl homoserine (thiol)-lyase, and homoserine kinase is inactivated.

9. The O-succinyl homoserine-producing microorganism of claim 5, wherein the microorganism overexpresses an aspartokinase, and one or more genes encoding cystathionine synthase, O-acetyl homoserine (thiol)-lyase, and homoserine kinase is inactivated.

10. A method of producing O-succinyl homoserine, the method comprising the steps of:
culturing the O-succinyl homoserine-producing microorganism of claim 5 in a medium to produce O-succinyl homoserine; and isolating or collecting the O-succinyl homoserine from the microorganism or the medium.

11. A method of producing L-methionine, the method comprising the steps of:
(a) culturing the O-succinyl homoserine-producing microorganism of claim 5 in a medium to produce O-succinyl homoserine; and
(b) reacting the O-succinyl homoserine with sulfide to produce L-methionine.

12. The method of producing L-methionine of claim 11, further comprising the step of isolating or collecting the O-succinyl homoserine from the microorganism or the medium.

13. The method of producing L-methionine of claim 11, further comprising the step of isolating or collecting the L-methionine.

* * * * *